(12) United States Patent
Begovich et al.

(10) Patent No.: US 6,656,691 B2
(45) Date of Patent: Dec. 2, 2003

(54) TCF-1 NUCLEOTIDE SEQUENCE VARIATION

(75) Inventors: Ann Bethea Begovich, El Cerrito, CA (US); Henry Anthony Erlich, Oakland, CA (US); Andrew Grupe, Redwood City, CA (US); Janelle Annette Noble, Berkeley, CA (US); Gary Allen Peltz, Redwood City, CA (US); Rebecca Lynne Reynolds, Milford, MA (US); Karen Myra Walker, Alameda, CA (US); Gabriele Zangenberg, Tutzing (DE)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 09/904,420

(22) Filed: Jul. 12, 2001

(65) Prior Publication Data

US 2003/0054350 A1 Mar. 20, 2003

Related U.S. Application Data

(60) Provisional application No. 60/219,812, filed on Jul. 21, 2000.

(51) Int. Cl.$^7$ .................. C07H 21/02; C07H 21/04; C12Q 1/68; C12P 19/34
(52) U.S. Cl. .................. 435/6; 435/91.2; 536/23.1; 536/23.5; 536/24.31; 536/24.33
(58) Field of Search .................. 435/6, 91.2; 536/23.1, 536/23.5, 23.7, 24.31, 24.33

(56) References Cited

PUBLICATIONS

USB Catalog of Molecular Biology Reagents. 1990. p. 166.*
Van De Wetering et al. "Extensive Alternative Splicing and Dual Promoter Usage Generate Tcf–1 Protein Isoforms with Differential Transcription Control Properties", *Molecular and Cellular Biology*, 16(3):745–752, 1996.
Van De Wetering et al. "The Human T Cell Transcription Factor–1 Gene", *Journal of Biological Chemistry*, 267(12):8530–8536, 1992.
Oksenberg et al. "Genetic Factors in Multiple Sclerosis", *JAMA*, 270():2362–2369, 1993.
Noble et al. "The Role of HLA Class II Genes in Insulin Dependent Diabetes Mellitus: Molecular Analysis of 180 Caucasian, Multiplex Families", *AM J Human Genetics*, 59():1134–1148, 1996.
Moffat et al. "Genetic Linkage of T–Cell Receptor α/δ Complex to Specific IgE Responses", *Lancet*, 343():1597–1600, 1994.
Daniels et al. "A Genome Wide Search for Quantitative Trait Loci Underlying Asthma", *Nature*, 383(19):247–250, 1996.
Genbank Accession No: 36791, 1992.

* cited by examiner

*Primary Examiner*—Carla J. Myers
(74) *Attorney, Agent, or Firm*—Pennie & Edmonds LLP

(57) ABSTRACT

Methods and reagents for determining sequence variants present at the TCF-1 locus, which facilitates identifying individuals at risk for Th1 diseases, such as type 1 diabetes or multiple sclerosis, or Th2 diseases, such as allergic asthma or atopy.

11 Claims, No Drawings

TCF-1 NUCLEOTIDE SEQUENCE VARIATION

This application claims priority under 35 U.S.C.§119(e) of provisional application Ser. No. 60/219,812, filed Jul. 21, 2000, which is incorporated herein by reference.

BACKGROUND OF THE INVENTION

Field of the Invention

The present invention relates to the fields of immunology and molecular biology. More specifically, it relates to methods and reagents for detecting nucleotide sequence variability in the TCF-1 locus that may be associated with risk of developing a Th1- or Th2-mediated inflammatory disease.

DESCRIPTION OF RELATED ART

CD4+ T lymphocytes have been divided into two functionally distinct subsets based on the pattern of cytokines secreted. One subset, designated T helper type 1 (Th1), secrete interleukin 2 (IL-2), IL-12, tumor necrosis factor (TNF), lymphotoxin (LT), and interferon gamma (IFN-γ) upon activation, and are primarily responsible for cell-mediated immunity such as delayed-type hypersensitivity. A second subset, designated T helper type 2 (Th2), secrete IL-4, IL-5, IL-6, IL-9, and IL-13 upon activation, and are primarily responsible for extracellular defense mechanisms. Stimulation of Th2-type lymphocytes results in secretion of lymphokines that induce B cells to produce antibodies and stimulate an increase in eosinophilic cells and IgE production, which results in an increase in mast cells, the release of histamines, and an inflammatory reaction. The role of Th1 and Th2 cells is reviewed in Peltz, 1991, Immunological Reviews 123: 23–35, incorporated herein by reference.

The immunological response to an antigen is mediated through the selective differentiation of CD4+ T helper precursor cells (Th0) to Th1 or Th2 effector cells, with their distinct patterns of lymphokine production. The secretion of the lymphokine subsets further provides a regulatory function in the differentiation of Th0 to Th1 or Th2 effector cells. For example, a lymphokine produced by Th2 cells, IL-4, both promotes the differentiation into Th2 cells and inhibits differentiation into Th1 cells. Conversely, lymphokines produced by Th1 cells, IL-12 and IFN-γ, promote differentiation into Th1 cells, inhibit differentiation into Th2 cells, and suppress IgE synthesis through direct effect on B cells. The reciprocal regulatory effects of the subset-specific lymphokines are involved in the polarization of Th1 or Th2 response.

Human T cells, upon activation in response to antigens involved in the pathogenesis of several chronic inflammatory or allergic diseases, exhibit a selective pattern of lymphokine production characteristic of Th1 or Th2-type cells. Certain autoimmune diseases, such as type 1 diabetes or multiple sclerosis (MS), have been shown to be associated with a predominant Th1 response. Th1-like pattern of lymphokine expression is seen in allergen-specific T cells isolated from patients with chronic Lyme arthritis and in patients with tuberculoid leprosy. In contrast, a Th2-like response of lymphokine expression is seen in allergen-specific T cells isolated from atopic patients. Most of the characteristic features of atopy and asthma, especially IgE synthesis, result from the combined effects of the cytokines secreted from Th2 cells.

It is likely that a selective imbalance or inappropriate activation of Th1 or Th2 T-cell subsets is central to the pathogenesis of certain chronic inflammatory or allergic diseases. Why the immune response of certain individuals to a pathogen or allergen is a protective response, while the immune response of others leads to disease, remains unclear. However, the probability that an individual will develop an inflammatory or allergic disease in response to exposure to a pathogen or allergen may be determined by the type of CD4+ T cell which dominates the response. An immune-mediated disease may develop if the cellular response becomes pathologically fixed in a Th1 or Th2 mode. The ability to clear or resolve a viral infection also may reflect a Th1, rather than a Th2, response.

Genetically determined differences in T-cell differentiation may determine the nature of the T cell response to an antigen, and thus whether there are pathogenic or non-pathogenic consequences. Although the control of T cell differentiation remains to be elucidated, many components of the cascade-like system of genes that control T cell differentiation have been—identified. T cell-specific transcription factor TCF-1 (now officially referred to as TCF-7) is one component of the system of genes that control T cell differentiation. The TCF-1 gene has been cloned and the sequence and structure have been described (see van der Wetering et al., 1992, J. Biol. Chem. 267 (12):8530–8536; van der Wetering et al., 1996, Molecular and Cellular Biology 16(3):745–752; both incorporated herein by reference).

SUMMARY OF INVENTION

The present invention relates to a newly discovered nucleotide sequence polymorphism in exon 2 of the TCF-1 gene and the association of the sequence variants with Th1- and Th2-mediated inflammatory diseases. Identification of the allelic sequence variant(s) present provides information regarding the immune system that may assist in characterizing individuals according to their risk of a disease in which the immune system is a factor, such as an inflammatory disease.

Two allelic sequence variants, which differ by the nucleotide present at nucleotide position 883 of the TCF-1 gene, have been identified. One aspect of the invention relates to genotyping with respect to the sequence variant present at nucleotide position 883.

The TCF-1 allelic differences appear to be associated with the likelihood of a Th1- or Th2-mediated inflammatory disease. As TCF-1 is a component of the system of genes that control T cell differentiation, and genetically determined differences in T-cell differentiation may determine the nature of the T cell response to an antigen, and thus whether there are pathogenic or non-pathogenic consequences, it is expected that allelic differences in the TCF-1 gene may affect T-cell differentiation. The association of the TCF-1 allelic differences with the likelihood of a Th1- or Th2-mediated inflammatory disease suggests that TCF-1 allelic differences may be a factor in determining the tendency of a Th1- or Th2-type response. It appears that one of the alleles may be associated with an increased tendency for a Th1-type response in response to an antigen, whereas the other allele may be associated with an increased tendency for a Th2-type response. Thus, the genotyping methods of the present invention provide information regarding a factor that may be relevant to classifying an individual according to their relative tendency to respond to an antigen with a Th1 response or a Th2 response.

As noted above, the probability that an individual will develop an inflammatory or allergic disease in response to exposure to a pathogen or allergen may be determined by the nature of the T cell response. By providing information on the tendency of an individual to respond to an antigen with a Th1 response or a Th2 response, the present invention provides information regarding the individual's immune system that may be relevant to classifying an individual's relative risk of a Th1- or Th2-mediated disease. Thus, the genotyping methods of the present invention provide information regarding a factor that may be relevant to classifying an individual as at increased risk for either a Th1- or Th2-mediated disease.

In particular embodiments, the genotyping methods of the present invention may provide information useful for assessing an individual's risk for particular Th1-mediated diseases, such as multiple sclerosis and type 1 diabetes, or Th2-mediated diseases, such as asthma and atopy. Individuals who have at least one "A" allele possess a factor contributing to the risk of a Th1-mediated disease. Individuals who have at least one "C" allele possess a factor contributing to the risk of a Th2-mediated disease.

As TCF-1 is one component of the complex system of genes that control T cell differentiation, and numerous other genes are involved in an immune response, the TCF-1 genotype on the immune response is one of a number of components which determine the nature of the T cell response and the likelihood of a Th1- or Th2-mediated disease. Consequently, the effect of the TCF-1 locus is expected to be small. Other factors, such as an individual's HLA genotype, may exert dominating effects which, in some cases, may mask the effect of the TCF-1 genotype. For example, particular HLA genotypes are known to have a major effect on the likelihood of type 1 diabetes (see Noble et al., 1996, Am. J. Hum. Genet. 59:1134–1148, incorporated herein by reference). The TCF-1 genotype is likely to be more informative as an indicator of predisposition towards type 1 diabetes among individuals who have HLA genotypes that confer neither increased nor decreased risk. It is expected that such dominating effects will be seen in other immune-mediated diseases, and a similar stratification of individuals is expected to be useful in such cases. Furthermore, because allele frequencies at other loci relevant to immune system-related diseases differ between populations and, thus, populations exhibit different risks for immune system-related diseases, it is expected that the effect of the TCF-1 genotype may not be apparent in all populations. Although the contribution of the TCF-1 genotype may be relatively minor by itself, genotyping at the TCF-1 locus will contribute information that is, nevertheless, useful for a characterization of an individual's predisposition towards either Th1- or Th2-mediated diseases. The TCF-1 genotype information may be particularly useful when combined with genotype information from other loci.

The present invention provides preferred methods, reagents, and kits for genotyping with respect to the sequence variant present at nucleotide position 883. The genotype can be determined using any method capable of identifying the nucleotide present at a single nucleotide polymorphic site. The particular method used is not a critical aspect of the invention. A number of suitable methods are described below.

In a preferred embodiment of the invention, genotyping is carried out using oligonucleotide probes specific to one or the other variant sequence. Preferably, a region of the TCF-1 gene which encompasses the probe hybridization region is amplified prior to, or concurrent with, the probe hybridization. An oligonucleotide specific for one of the variant sequences is exactly or substantially complementary to either strand of a TCF-1 gene in a region of the gene which encompasses the polymorphic site, and is exactly complementary at the polymorphic site to one of the variant sequences. Probe-based assays are well known in the art.

Alternatively, genotyping is carried out using an allele-specific amplification or extension reaction, wherein an allele-specific primer is used which supports primer extension only if the targeted variant sequence is present. Typically, an allele-specific primer hybridizes to the TCF-1 gene such that the 3' terminal nucleotide aligns with the polymorphic position. Allele-specific amplification reactions and allele-specific extension reactions are well known in the art.

Another aspect of the invention relates to oligonucleotides useful as amplification primers, detection probes, or positive control sequences which are added to reactions to provide a known target sequence. For use as a positive control sequence, the oligonucleotide is preferably contained in a DNA vector such as a plasmid. For use in sequence-specific amplification or detection, the oligonucleotide preferably is about 10 to about 35 nucleotides in length, more preferably about 15 to about 35 nucleotides in length.

Another aspect of the invention relates to kits useful for genotyping with respect to the sequence variant present at nucleotide position 883 of the TCF-1 gene. These kits take a variety of forms, but in each case contain one or more reagents for carrying out the genotyping methods of the invention, such as an oligonucleotide which is specific for one of the sequence variants. The kits can also comprise one or more amplification reagents, e.g., primers, polymerase, buffers, and nucleoside triphosphates.

DETAILED DESCRIPTION OF THE INVENTION

The term "TCF-1 gene" refers to the genomic nucleic acid sequence that encodes the T cell-specific transcription factor protein, specifically, the gene sequence available from GenBank under accession number X63901 and shown in Table 1, and allelic variants thereof. The nucleotide sequence of the gene, as used herein, encompasses both coding regions, referred to as exons, and intervening, non-coding regions, referred to as introns.

The term "allele" refers to a nucleotide sequence variant of the gene.

As used herein, a "C allele" refers to a nucleotide sequence variant of the gene. As used herein, a "C allele" refers to sequence variants that contain a cytosine at the polymorphic position which is nucleotide position 883 of the TCF-1 gene strand shown in Table 1. As used herein, an "A allele" refers to sequence variants that contain an adenosine at nucleotide position 883 of the TCF-1 gene strand shown in Table 1. It will be clear that in a double stranded form, the complementary strand of each allele will contain the complementary base at the polymorphic position.

The term "genotype" refers to a description of the alleles of a gene contained in an individual or a sample. As used herein, no distinction is made between the genotype of an individual and the genotype of a sample originating from the individual. Although, typically, a genotype is determined from samples of diploid cells, a genotype can be determined from a sample of haploid cells, such as a sperm cell.

The terms "polymorphic" and "polymorphism", as used herein, refer to the condition in which two or more variants of a specific genomic sequence can be found in a population. The polymorphic region or polymorphic site refers to a region of the nucleic acid where the nucleotide difference distinguishing the variants occurs.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA and DNA/RNA hybrids.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference. Oligonucleotides typically are synthesized using reagents and instruments commercially available from, for example, PE Biosystems (Foster City, Calif.) and Pharmacia (Piscataway, N.J.). Methods for incorporating an oligonucleotide into a DNA vector, such as for use as a positive control target sequence, are well known in the art and described in references cited herein.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch, wherein the total number of mismatched nucleotides is no more than about 3 for sequences about 15 to about 35 nucloetides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from National Biosciences, Inc. (Plymouth, Minn.); the OLIGO version 5 reference manual is incorporated herein by reference.

Stringent, sequence-specific hybridization conditions, under which an oligonucleotide will hybridize only to the exactly complementary target sequence, are well known in the art (see, e.g., Sambrook et al., 1989, *Molecular Cloning—A Laboratory Manual*, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "probe" refers to an oligonucleotide which is capable of selectively hybridizing to a target nucleic acid under suitable conditions. The probe will contain a "hybridizing region" exactly or substantially complementary to the target sequence, and will be exactly complementary to the target sequence at a polymorphic site. A hybridization assay carried out using the probe under sufficiently stringent hybridization conditions enables the selective detection of a specific target sequence. For use in a hybridization assay for the discrimination of single nucleotide differences in sequence, the probe hybridizing region is preferably from about 10 to about 35 nucleotides in length, more preferably from about 15 to about 35 nucleotides in length. The use of modified bases or base analogues which affect the hybridization stability, which are well known in the art, may enable the use of shorter or longer probes with comparable stability. One of skill in the art will recognize that, in general, the exact complement of a given probe is equally useful as a probe. A probe oligonucleotide can either consist entirely of the hybridizing region or can contain additional features which allow for the detection or immobilization of the probe, but which do not significantly alter the hybridization characteristics of the hybridizing region. For example, the probe hybridizing region may be bound to a poly-T "tail", which is used to immobilize the probe to a solid support for use in the reverse dot-blot assay.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer will contain a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the basic property of the primer, that of acting as a point of initiation of DNA synthesis. For example, to facilitate cloning of the amplified product, a short nucleic acid sequence which contains a restriction enzyme cleavage site can be bound to the 5' end of the primer.

An "allele-specific" primer, as used herein, is a primer that hybridizes to the target sequence such that the 3' end of the primer aligns with the polymorphic site that defines the alleles (i.e., position 883 for the TCF-1 A and C alleles) and is exactly complementary to one of the alleles at the polymorphic position. The primer is "specific for" the allele to which it is exactly complementary at the 3' end. In general, primer extension, which occurs at the 3' end of the primer, is inhibited by a mismatch at the 3' end of a primer. An allele-specific primer, when hybridized to the exactly complementary allele, is extendable. However, the same primer, when hybridized to the other allele, is not extendable because of the mismatch at the 3' end of the primer in the hybridization duplex. Thus, the use of an allele-specific primer enables allelic discrimination based on whether amplification product is formed.

The term "target region" refers to a region of a nucleic acid which is to be analyzed and usually includes a polymorphic region.

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); the series, Methods in Enzymology (Academic Press, Inc.); and the series, Current Protocols in Human Genetics (Dracopoli et al., eds., 1984 with quarterly updates, John Wiley & Sons, Inc.); all of which are incorporated herein by reference. All patents, patent applications, and publications mentioned herein, both supra and infra, are incorporated herein by reference.

TCF-1 Gene Nucleotide Sequence

The nucleotide sequence of a complete C allele of the TCF-1 gene is available from GenBank under accession number X63901 and provided as SEQ ID NO: 1, shown in a 5' to 3' orientation in Table 1, below. The newly discovered single nucleotide polymorphism occurs at position 883, shown highlighted. The sequence variant that defines the A allele consists of the substitution at this position of an "A" for the "C" present in SEQ ID NO: 1. A C to A substitution at this position corresponds to a change in the encoded amino acid from proline to threonine.

Although only one strand of the nucleic acid is shown in Table 1, those of skill in the art will recognize that SEQ ID NO: 1 identifies a region of double-stranded genomic nucleic acid, and that the sequences of both strands are fully specified by the sequence information provided.

TABLE 1

| SEQ ID NO:1 |
| --- |
| 1 GGATCCCGGG GGTCCCGGGG GCCGGCGCCG GGGCCCGCGG CGAGGCCGAG GTGAGCCCCC |
| 61 GCCGGCGCCC GCTCCTCCCC CGCGGTCGCC GCCCGCGCCG CCCCAGTTGC GCGCCGCCCT |
| 121 CGGGGTCTCG AGACAGAGCG TCCCTGCCCC GGCGTCGGCC CCGACCCCCG CGGTCCCACC |
| 181 GCCCCTCACT CCCCTCCGGT TCTCCCTCCA GGCTCTCGGG CGGGAACACC GTGCGCAGAG |
| 241 ACTCTTCCCG GACAAACTTC CAGAGCCCCT GGAGGACGGT GAGTTTCTGC CCGGCCCGGC |
| 301 TTCCCTTCGT CGCGCTCAGG CCCTGGCCTC GGTGGGACGG GGACGCCAAG GACCGCGGGG |
| 361 AGCCGGGTGC CTCCCCCACC GCAGCTCAGG AGGCGGCAGA ACCCAGGGGT GGAGAGTGGG |
| 421 GGGCGNGCTT CCCGGGCGCC GCCGGGTCGA GTCACTTCCG GTGCCCTGAC CTTTATAGGA |
| 481 GTAAACAGAC CCCCGCCATC CCCGCCTCCC CTCCTGCCCA GGTGACTGAC TAATCCGCCG |
| 541 CCTTCAGGAG ACAGAATTGG CCAAGGTTTC TTGGTTGGAG GGTGGGGGGT GGGAGGTCAA |
| 601 GTAGGGGCCA CCTCGGGGAG GCCTGCCCTC CAGGTCCTTC CCCTAAAACT TGCCACTGCC |
| 661 GATACTCCCA GCCCGTTCCT TCCCAAGTCA GGAACTTGCA GGGGACCCCT TGGCAATTCT |
| 721 TTTTCTCTCA AGAGCAGACA GCCTTCAGTC CCAGCCGCTG CCAGGGCTGG TGTGTCTGAC |
| 781 CCAGCTGTGG TTTTTCCAGG CCTGAAGGCC CCGGAGTGCA CCAGGGGCAT GTACAAAGAG |
| 841 ACCGTCTACT CCGCCTTCAA TCTGCTCATG CATTACCCAC CCCCCTCGGG AGCAGGGCAG |
| 901 CACCCCCAGC CGCAGCCCCC GCTGGTAAGT GGACCCCGCC ACTCACCCAC CCTCCTTCTC |
| 961 ATTTTTCAGC ACAAGGCCAA TCAGCCCCCC CACGGTGTCC CCCAACTCTC TCTCTACGAA |
| 1021 CATTTCAACA GCCCACATCC CACCCCTGCA CCTGCGGACA TCAGCCAGAA GCAAGGTACA |
| 1081 AGCCTGGGAT GCCCACTCAC TCAGCTTCTC TCCTCTGCAG TTCACAGGCC TCTGCAGACC |
| 1141 CCTGACCTCT CTGGCTTCTA CTCCCTGACC TCAGGCAGCA TGGGCCAGCT CCCCCACACT |
| 1201 GTGAGCTGGT GAGTGTGGGC CCAGCTCAGT GTTAACTTTC TTCCTGCCTC CAGGTTCACC |
| 1261 CACCCATCCT TGATGCTAGG TTCTGGTGTA CCTGGTCACC CAGCAGCCAT CCCCCACCCG |
| 1321 GCCATTGTGC CCCCCTCAGG GAAGCAGGAG CTGCAGCCCT TCGACCGCAA CCTGTGAGTG |
| 1381 AAAGACAATC CTGAACAATC TGGATTTGTG CCCCTCAGGA AGACACAAGC AGAGTCCAAG |
| 1441 GCAGAGAAGG AGGCCAAGAA GCCAACCATC AAGAAGCCCC TCAATGCCTT CATGCTGTAC |
| 1501 ATGAAGGAGA TGAGAGCCAA GGTCATTGCA GAGTGCACAC TTAAGGAGAG CGCTGCCATC |
| 1561 AACCAGATCC TGGGCCGCAG GGTGAGACCA TGGGCAGGTG GGCTGGCAGG GATGCTCCCC |

TABLE 1-continued

SEQ ID NO:1

```
1621 GACCATCTTC AGCCTGGTGC AGCCTGCTGA CTCCCTGATG CACCCCACCT GCCCCTCTTC

1681 CCTGTTGCAG TGGCACGCGC TGTCGCGAGA AGAGCAGGCC AAGTACTATG AGCTGGCCCG

1741 CAAGGAGAGG CAGCTGCACA TGCAGCTATA CCCAGGCTGG TCAGCGCGGG ACAACTACGT

1801 GAGTGCCTAG TGTCTGAGCA TCCCTCCTTT TGTTCCCTGC AGGGGAAGAA GAAGAGGCGG

1861 TCGAGGGAAA AGCACCAAGA ATCCACCACA GGTGAGACCT TCTCTCGCTC TACCCCTCTG

1921 GCATGGCTGT GAGCAGACCC TGGCTCGCCT AAGAAATGCC GTGCTCGCTT TGGCCTCAAC

1981 CAGCAGACGG ATTGGTGTGG TCCGTGCAGG TGGGTTTGTC CCCAGGGGAA GTTCTATTCC

2041 ATTCATTCCA TCAGAGACAA ACTGGCCCAG AGAACTCAAG GATGGTAATG GACAAGAGTC

2101 ACTGTCCATG TCTTCTTCCT CTAGCCCAGC TTGAGGACTG GGATGGCTGG GCAAGGAAGC

2161 CATAGGCATT GCGGCCCCTT GCCTTGGTGC AGATGTGAGT CCCACAAACA CATCTGGAGA

2221 AGCTCAAAGG CCGGGACTGG GAGATGACTC CCTTGGAAGA CAGGAGAGAT GACTCCCTTG

2281 GAAGACAGAT GACAGCCCAT AGGCCTAGTG ACAAAAGGCC CCTTTGGGAC CTTGTGGCTG

2341 TTCTGGGAAC TGCACCTGTC CTAGGTCTGG GCCAGACCAA GCAGAATGGC AGTCTGAGGA

2401 CACTGACTTA CCACCCAAGT CCCAGGAAGA GAGGACAAGG AATCAGCCAG GCCTGTGCAA

2461 AGGCAGCATT TTTTGGTTGT GGTGTATGAC TATGAATTCA CCCTCTGTTT ACAGATAACT

2521 CTCTTCACTA TTCCTAGGAG GAAAAAGAAA TGCATTCGGT ACTTACCCGG AGAAGGCCGC

2581 TGCCCCAGCC CCGTTCCTTC CGATGACAGT GCTCTAGGCT GCCCCGGGTC CCCAGCTCCC

2641 CAGGACTCAC CCTCATACCA TCTGCTGCCC CGCTTCCCCA CAGAACTGCT TACTAGCCCT

2701 GAAAAAGATT ATTGTAGTGT TCAAAATATT TTTGTATTGT TAATGCATCA TCATAGAAAA

2761 ACTTTTAAAC ATGAGAATAA AGATACTTTT TACTGGGTTT GTTTTTCAAA GCCTGACCCT

2821 GAGGAATAAG CTGTTTCAGT AACAGAGCAT GATAT
```

Genotyping Methods

In the methods of the present invention, the alleles present in a sample are identified by identifying the nucleotide present at the polymorphic site, nucleotide position 883 of SEQ ID NO: 1. Any type of tissue containing TCF-1 nucleic acid may be used for determining the TCF-1 genotype of an individual. A number of methods are known in the art for identifying the nucleotide present at a single nucleotide polymorphism. The particular method used to identify the genotype is not a critical aspect of the invention. Although considerations of performance, cost, and convenience will make particular methods more desirable than others, it will be clear that any method that can identify the nucleotide present will provide the information needed to identify the genotype. Preferred genotyping methods involve DNA sequencing, allele-specific amplification, or probe-based detection of amplified nucleic acid.

TCF-1 alleles can be identified by DNA sequencing methods, such as the chain termination method (Sanger et al., 1977, *Proc. Natl. Acad. Sci.* 74:5463–5467, incorporated herein by reference), which are well known in the art. In one embodiment, a subsequence of the gene encompassing the polymorphic site is amplified and either cloned into a suitable plasmid and then sequenced, or sequenced directly. PCR-based sequencing is described in U.S. Pat. No. 5,075,216; Brow, in PCR Protocols, 1990, (Innis et al., eds., Academic Press, San Diego), chapter 24; and Gyllensten, in PCR Technology, 1989 (Erlich, ed., Stockton Press, New York), chapter 5; each incorporated herein by reference. Typically, sequencing is carried out using one of the automated DNA sequencers which are commercially available from, for example, PE Biosystems (Foster City, Calif.), Pharmacia (Piscataway, N.J.), Genomyx Corp. (Foster City, Calif.), LI-COR Biotech (Lincloln, Nebr.), GeneSys technologies (Sauk City, Wis.), and Visable Genetics, Inc. (Toronto, Canada).

TCF-1 alleles can be identified using amplification-based genotyping methods. A number of nucleic acid amplification methods have been described which can be used in assays capable of detecting single base changes in a target nucleic acid. A preferred method is the polymerase chain reaction (PCR), which is now well known in the art, and described in U.S. Pat. Nos. 4,683,195; 4,683,202; and 4,965,188; each incorporated herein by reference. Examples of the numerous articles published describing methods and applications of PCR are found in PCR Applications, 1999, (Innis et al., eds., Academic Press, San Diego), PCR Strategies, 1995, (Innis et al., eds., Academic Press, San Diego); PCR Protocols, 1990, (Innis et al., eds., Academic Press, San Diego); and PCR Technology, 1989, (Erlich, ed., Stockton Press, New York); each incorporated herein by reference. Commercial vendors, such as PE Biosystems (Foster City, Calif.) market PCR reagents and publish PCR protocols.

Other suitable amplification methods include the ligase chain reaction (Wu and Wallace 1988, Genomics 4:560–569); the strand displacement assay (Walker et al., 1992, *Proc. Natl. Acad. Sci. USA* 89:392–396, Walker et al. 1992, Nucleic Acids Res. 20:1691–1696, and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, *Proc. Natl. Acad. Sci. USA* 86:1173–1177); and self-sustained sequence replication (3 SR) (Guatelli et al., 1990, *Proc. Natl. Acad. Sci. USA* 87:1874–1878 and WO 92/08800); each incorporated herein by reference. Alternatively, methods that amplify the probe to detectable levels can be used, such as QB-replicase amplification (Kramer and Lizardi, 1989, *Nature* 339:401–402, and Lomeli et al., 1989, *Clin. Chem.* 35:1826–1831, both of which are incorporated herein by reference). A review of known amplification methods is provided in Abramson and Myers, 1993, *Current Opinion in Biotechnology* 4:41–47, incorporated herein by reference.

Genotyping also can be carried out by detecting TCF-1 mRNA. Amplification of RNA can be carried out by first reverse-transcribing the target RNA using, for example, a viral reverse transcriptase, and then amplifying the resulting cDNA, or using a combined high-temperature reverse-transcription-polymerase chain reaction (RT-PCR), as described in U.S. Pat. Nos. 5,310,652; 5,322,770; 5,561,058; 5,641,864; and 5,693,517; each incorporated herein by reference (see also Myers and Sigua, 1995, in PCR Strategies, supra, chapter 5).

TCF-1 alleles can be identified using allele-specific amplification or primer extension methods, which are based on the inhibitory effect of a terminal primer mismatch on the ability of a DNA polymerase to extend the primer. To detect an allele sequence using an allele-specific amplification- or extension-based method, a primer complementary to the TCF-1 gene is chosen such that the 3' terminal nucleotide hybridizes at the polymorphic position. In the presence of the allele to be identified, the primer matches the target sequence at the 3' terminus and primer is extended. In the presence of only the other allele, the primer has a 3' mismatch relative to the target sequence and primer extension is either eliminated or significantly reduced. Allele-specific amplification- or extension-based methods are described in, for example, U.S. Pat. Nos. 5,137,806; 5,595,890; 5,639,611; and U.S. Pat. No. 4,851,331, each incorporated herein by reference. A preferred allele-specific amplification-based method of genotyping is described in the examples.

Alternatively, sequence-specific amplification can be carried out using a primer which hybridizes to a region encompassing the polymorphic site and is exactly complementary to one allele by selecting conditions under which a stable hybridization duplex is formed only between the primer and the perfectly matched allele. Such methods are less preferred for distinguishing single nucleotide polymorphisms due to the difficulty of eliminating partial hybridization of the primer to mismatched allele, which results in the generation of an unintended amplification product. In contrast, methods based on the presence of a 3' terminal mismatch discriminate between alleles even if the primer hybridizes to both alleles.

Using allele-specific amplification-based genotyping, identification of the alleles requires only detection of the presence or absence of amplified target sequences. Methods for the detection of amplified target sequences are well known in the art. For example, gel electrophoresis (see Sambrook et al., 1989, supra.) and the probe hybridization assays described above have been used widely to detect the presence of nucleic acids.

An alternative probe-less method, referred to herein as a kinetic-PCR method, in which the generation of amplified nucleic acid is detected by monitoring the increase in the total amount of double-stranded DNA in the reaction mixture, is described in Higuchi et al., 1992, *Bio/Technology* 10:413–417; Higuchi et al., 1993, *Bio/Technology* 11:1026–1030; Higuchi and Watson, in PCR Applications, supra, Chapter 16; U.S. Pat. No. 5,994,056; and European Patent Publication Nos. 487,218 and 512,334, each incorporated herein by reference. The detection of double-stranded target DNA relies on the increased fluorescence that ethidium bromide (EtBr) and other DNA-binding dyes exhibit when bound to double-stranded DNA. The increase of double-stranded DNA resulting from the synthesis of target sequences results in an increase in the amount of dye bound to double-stranded DNA and a concomitant detectable increase in fluorescence. For genotyping using the kinetic-PCR methods, amplification reactions are carried out using a pair of primers specific for one of the alleles, such that each amplification can indicate the presence of a particular allele. By carrying out two amplifications, one using primers specific for the A allele and one using primers specific for the C allele, the genotype of the sample can be determined.

A preferred allele-specific amplification-based method is described in the examples in which allele-specific multiple primers are used in a single reaction. The primers are selected such that the amplification products produced from the alleles are distinguishable by size. Thus, both alleles in a single sample can be identified using a single amplification by gel analysis of the amplification product.

Alleles can be identified using probe-based methods, which rely on the difference in stability of hybridization duplexes formed between the probe and the TCF-1 alleles, which differ in the degree of complementarity. Under sufficiently stringent hybridization conditions, stable duplexes are formed only between the probe and the target allele sequence. The presence of stable hybridization duplexes can be detected by any of a number of well known methods. In general, it is preferable to amplify the nucleic acid prior to hybridization in order to facilitate detection. However, this is not necessary if sufficient nucleic acid can be obtained without amplification.

In one embodiment, the nucleotide present at the polymorphic site is identified by hybridization under sequence-specific hybridization conditions with an oligonucleotide probe exactly complementary to one of the TCF-1 alleles in a region encompassing the polymorphic site. The probe hybridizing sequence and sequence-specific hybridization conditions are selected such that a single mismatch at the polymorphic site destabilizes the hybridization duplex sufficiently so that it is effectively not formed. Thus, under sequence-specific hybridization conditions, stable duplexes will form only between the probe and the exactly complementary allelic sequence. Thus, oligonucleotides from about 10 to about 35 nucleotides in length, preferably from about 15 to about 35 nucleotides in length, which are exactly complementary to an allele sequence in a region which encompasses the polymorphic site are within the scope of the invention.

In an alternative embodiment, the nucleotide present at the polymorphic site is identified by hybridization under sufficiently stringent hybridization conditions with an oligonucleotide substantially complementary to one of the TCF-1 alleles in a region encompassing the polymorphic site, and exactly complementary to the allele at the polymorphic site. Because mismatches which occur at non-polymorphic sites are mismatches with both allele sequences, the difference in the number of mismatches in a duplex formed with the target allele sequence and in a duplex formed with the corresponding non-target allele sequence is the same as when an oligonucleotide exactly complementary to the target allele sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, stable duplexes will form only between the probe and the target allele. Thus, oligonucleotides from about 10 to about 35 nucleotides in length, preferably from about 15 to about 35 nucleotides in length, which are substantially complementary to an allele sequence in a region which encompasses the polymorphic site, and are exactly complementary to the allele sequence at the polymorphic site, are within the scope of the invention.

The use of substantially, rather than exactly, complementary oligonucleotides may be desirable in assay formats in which optimization of hybridization conditions is limited. For example, in a typical multi-target immobilized-probe assay format, probes for each target are immobilized on a single solid support. Hybridizations are carried out simultaneously by contacting the solid support with a solution containing target DNA. As all hybridizations are carried out under identical conditions, the hybridization conditions cannot be separately optimized for each probe. The incorporation of mismatches into a probe can be used to adjust duplex stability when the assay format precludes adjusting the hybridization conditions. The effect of a particular introduced mismatch on duplex stability is well known, and the duplex stability can be routinely both estimated and empirically determined, as described above.

A probe suitable for use in the probe-based methods of the present invention, which contains a hybridizing region either substantially complementary or exactly complementary to a target region of SEQ ID NO: 1 or the complement of SEQ ID NO: 1, wherein the target region encompasses the polymorphic site, and exactly complementary to one of the two allele sequences at the polymorphic site, can be selected using the guidance provided herein and well known in the art. Similarly, suitable hybridization conditions, which depend on the exact size and sequence of the probe, can be selected empirically using the guidance provided herein and well known in the art. The use of oligonucleotide probes to detect single base pair differences in sequence is described in, for example, Conner et al., 1983, *Proc. Natl. Acad. Sci. USA* 80:278–282, and U.S. Pat. Nos. 5,468,613 and 5,604,099, each incorporated herein by reference.

The proportional change in stability between a perfectly matched and a single-base mismatched hybridization duplex depends on the length of the hybridized oligonucleotides. Duplexes formed with shorter probes sequences are destabilized proportionally more by the presence of a mismatch. In practice, oligonucleotides between about 15 and about 35 nucleotides in length are preferred for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the polymorphic site occurs in the interior region of the probe.

The above criteria for selecting a probe sequence which hybridizes to SEQ ID NO: 1 apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

In preferred embodiments of the probe-based methods for determining the TCF-1 genotype, a nucleic acid sequence from the TCF-1 gene which encompasses the polymorphic site is amplified and hybridized to the probes under sufficiently stringent hybridization conditions. The TCF-1 alleles present are inferred from the pattern of binding of the probes to the amplified target sequence. In this embodiMant, amplification is carried out in order to provide sufficient nucleic acid for analysis by probe hybridization. Thus, primers are designed such that a region of the TCF-1 gene encompassing the polymorphic site is amplified regardless of the allele present in the sample. Allele-independent amplification is achieved using primers which hybridize to conserved regions of the TCF-1 gene. The TCF-1 gene sequence is highly conserved and suitable allele-independent primers can be selected routinely from SEQ ID NO: 1. One of skill will recognize that, typically, experimental optimization of an amplification system is helpful.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

Probe-based genotyping can be carried out using a "TaqMan" or "5'-nuclease assay", as described in U.S. Pat. Nos. 5,210,015; 5,487,972; and 5,804,375; and Holland et al., 1988, Proc. Natl. Acad. Sci. USA 88:7276–7280, each incorporated herein by reference. In the TaqMan assay, labeled detection probes that hybridize within the amplified region are added during the amplification reaction mixture. The probes are modified so as to prevent the probes from acting as primers for DNA synthesis. The amplification is carried out using a DNA polymerase that possesses 5' to 3' exonuclease activity, e.g., Tth DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in the TaqMan assay. In a preferred method, the detection probes are labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

The TaqMan assay can be used with allele-specific amplification primers such that the probe is used only to detect the presence of amplified product. Such an assay is carried out as described for the kinetic-PCR-based methods described above. Alternatively, the TaqMan assay can be used with a target-specific probe.

The assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include $^{32}$P, fluorescent dyes, electron-dense reagents, enzymes (as commonly used in ELISAS), biotin, or haptens and proteins for which antisera or monoclonal antibodies are available. Labeled oligonucleotides of the invention can be synthesized and labeled using the techniques described above for synthesizing oligonucleotides. For example, a dot-blot assay can be carried out using probes labeled with biotin, as described in Levenson and Chang, 1989, in *PCR Protocols: A Guide to Methods and Applications* (Innis et al., eds., Academic Press. San Diego), pages 99–112, incorporated herein by reference. Following hybridization of the immobilized target DNA with the biotinylated probes under sequence-specific conditions, probes which remain bound are detected by first binding the biotin to avidin-horseradish peroxidase (A-HRP) or streptavidin-horseradish peroxidase (SA-HRP), which is then detected by carrying out a reaction in which the HRP catalyzes a color change of a chromogen.

Various other methods have been described which can be used for Genotyping. For example, TCF-1 alleles can be identified by changes in the mobility measured by gel electrophoresis. Typically, a small region of the TCF-1 allele encompassing the polymorphic site is amplified and the amplification product is analyzed by gel electrophoresis. Alternatively, fragments of the allele are generated by digestion with restriction enzymes and the fragments which encompass the polymorphic site are analyzed by gel electrophoresis. Gel-based methods for identifying single nucleotide changes in DNA are described in Sheffield et al., in PCR Protocols, 1990, (Innis et al., eds., Academic Press, San Diego), chapter 26, incorporated herein by reference.

The difference in mobility can be enhanced by selectively incorporating nucleotide analogs in the nucleic acid sequence at the polymorphic position. U.S. Pat. No. 4,879,214, incorporated herein by reference, describes a primer extension-based method in which a nucleotide analog is included such that the extension product formed using one of the alleles as a template incorporates the analog. The analog is selected such that it changes the mobility of the extended product, which facilitates distinguishing the extension products formed from the different alleles.

The selective incorporation of nucleotide analogs at the polymorphic position also can be used to render the extension product from one allele resistant to nuclease degradation. U.S. Pat. No. 4,656,127, incorporated herein by reference, describes a method in which a labeled DNA probe is hybridized to the target nucleic acid such that the 3' end of the probe is positioned adjacent to the position being analyzed. A nucleotide analog, such as a thionucleotide, is included in the extension reaction such that the analog is incorporated using only one of the alleles as template and not if the other allele is present as the template. The extended probe is resistant to cleavage with exonuclease III if the nucleotide analog was incorporated. Thus, the presence of undigested, labeled probe following treatment with exonuclease III indicates the presence of the specific allele.

Whatever the method for determining which oligonucleotides of the invention selectively hybridize to TCF-1 allelic sequences in a sample, the central feature of the typing method involves the identification of the TCF-1 alleles present in the sample by detecting the variant sequences present.

The present invention also relates to kits, container units comprising useful components for practicing the present method. A useful kit can contain oligonucleotide probes specific for the TCF-1 alleles. In some cases, detection probes may be fixed to an appropriate support membrane. The kit can also contain amplification primers for amplifying a region of the TCF-1 locus encompassing the polymorphic site, as such primers are useful in the preferred embodiment of the invention. Alternatively, useful kits can contain a set of primers comprising an allele-specific primer for the specific amplification of TCF-1 alleles. Other optional components of the kits include additional reagents used in the genotyping methods as described herein. For example, a kit additionally can contain an agent to catalyze the synthesis of primer extension products, substrate nucleoside triphosphates, means for labeling and/or detecting nucleic acid (for example, an avidin-enzyme conjugate and enzyme substrate and chromogen if the label is biotin), appropriate buffers for amplification or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Genotyping Protocol

Sequence-Specific Amplification-Based Identification of TCF-1 Alleles

The genotype of a human sample can be determined by sequence-specific amplifications using primers which distinguish the alleles based on the nucleotide present at position 883. In the following protocol, the genotype is determined by analyzing the pattern of amplification products generated using primers which amplify fragments of different lengths depending on the alleles present.

Amplification Primers

Amplifications are carried out using four primers, two of which are upstream primers and two of which are downstream primers. The sequences of preferred primers are shown below in a 5' to 3' orientation.

| Name | SEQ ID NO: | Sequence (5'-3') | 5'<br>Nucleotide |
|------|------------|------------------|------------------|
| GZ346B | 2 | CCAGGTCCTTCCCCTAA | 630 |
| LS045B | 3 | TCCAGGTCCTTCCCCTAAAA | 629 |
| GZ351B | 4 | CATGCATTACCCACCCA | 867 |
| GZ374B | 5 | CCTGCTCCCGAGGG | 896 |
| GZ348B | 6 | GCGGGGTCCACTTACCA | 939 |

Upstream primer LS045B (SEQ ID NO: 3) and downstream primer GZ348B (SEQ ID NO: 6) hybridize to a region spanning the single nucleotide polymorphism. Amplification using these two primers will result in the synthesis of a 311 base pair (bp) product regardless of the nucleotide present at the polymorphic position.

Primer GZ374B (SEQ ID NO: 5) is a downstream primer that hybridizes to the TCF-1 sequence such that the 3' terminal nucleotide hybridizes at the polymorphic site, position 883. Primer GZ374B (SEQ ID NO: 5) is exactly complementary to the C allele and, thus, has a 3' terminal mismatch relative to the A allele. Under suitable conditions, as described below, an amplification product is generated only if a C allele is present in the sample. Amplification using primers LS045B (SEQ ID NO: 3) and GZ374B (SEQ ID NO: 5) results in an amplification of a 268 bp nucleotide product if a C allele is present in the sample.

Primer GZ351B (SEQ ID NO: 4) is an upstream primer that hybridizes to the TCF-1 sequence such that the 3' terminal nucleotide hybridizes at the polymorphic site, position 883. Primer GZ351B (SEQ ID NO: 4) is exactly complementary to the A allele and, thus, has a 3' terminal mismatch relative to the C allele. Under suitable conditions, as described below, an amplification product is generated only if an A allele is present in the sample. An amplification using primers GZ351B (SEQ ID NO: 4) and GZ348B (SEQ ID NO: 6) results in an amplification of a 73 bp product only if an A allele is present in the sample.

Primer GZ346B (SEQ ID NO: 2) is an alternative upstream primer that can be used in place of primer LS045B (SEQ ID NO: 3) in the above pairings.

Using the above primers, SEQ ID NOs. 3–6, the products generated by amplifications of the possible genotypes are distinguishable. The possible amplification results are shown in the table, below.

| Product Size | Gentype AA | Genotype AC | Genotype CC |
|---|---|---|---|
| 73 bp | yes | yes | no |
| 268 bp | no | yes | yes |
| 311 bp | yes | yes | yes |

Amplification

The PCR amplification is carried out in a total reaction volume of 25–100 μl containing the following reagents:

0.2–1 ng/μl purified human genomic DNA
0.2 μM each of the four primers
800 μM total dNTP (200 μM of each dATP, dCTP, dGTP, dTTP)
60 mM KCl
12 mM Tris-HCl, pH 8.3
2.4 mM $MgCl_2$,
0.05–0.1 units/μl AmpliTaq Gold ™ DNA polymerase*

*developed and manufactured by Hoffmann-La Roche and commercially available from PE Biosystems (Foster City, CA).

Amplification is carried out in a GeneAmp® PCR System 9600 thermal cycler (PE Biosystems, Foster City, Calif.), using the specific temperature cycling profile shown below.

| Pre-reaction incubation: | 94° C. for 12 minutes |
|---|---|
| 37 cycles: | |
| denature: | 95° C. for 45 seconds |
| anneal: | 61° C. for 30 seconds |
| extend: | 72° C. for 30 seconds |
| Final extension: | 72° C. for 7 minutes |
| Hold: | 10° C.–15° C. |

Gel Electrophoretic Detection

Amplified DNA is size fractionated by agarose gel electrophoresis to determine the size of the amplified products. A 3% NuSieve/1.0% Agarose gel in 0.5× TBE (0.045 M Tris-borate and 0.001 M disodium EDTA) running buffer is used. Ethidium bromide (0.5 μg/ml) is added to both the gel and the running buffer (alternatively, staining may be carried out after electrophoresis).Electrophoresis is carried out at 100 volts for approximately 1 hour. The ethidium bromide stained bands of DNA are visualized using UV irradiation.

EXAMPLE 2

Genotyping Protocol

Probe-based Identification of TCF-1 Alleles

This example describes an alternative genotyping method. A region of the TCF-1 gene that encompasses the polymorphic site is amplified and the nucleotide present is identified by probe hybridization. The probe detection is carried out either using an immobilized target (dot-blot) format, or using an immobilized probe (reverse dot-blot or line blot) format.

Amplification Primers

Amplification of a region of the TCF-1 gene corresponding to nucleotides 847 to 939 of SEQ ID NO: 1, which encompasses the polymorphic site at position 883, is carried out using the upstream primer, RR328B (SEQ ID NO: 7), shown below, together with downstream primer GZ348B (SEQ ID NO: 6). The upstream primer sequence is shown in the 5'->3' orientation.

RR328B (SEQ ID NO:7) TACTCCGCCTTCAATCTGCTCA

For use in the immobilized probe detection format, described below, the primer which is incorporated into the strand complementary to the probe is labeled with biotin attached to the 5' phosphate, which facilitates detection. Reagents for synthesizing oligonucleotides with a biotin label attached to the 5' phosphate are commercially available from Clonetech (Palo Alto, Calif.) and Glenn Research (Sterling, Va.). A preferred reagent is Biotin-ON from Clonetech.

Amplification

The PCR amplification is carried out in a total reaction volume of 25–100 µl containing the following reagents:

```
0.2 ng/µl purified human genomic DNA
0.2 µM each primers
800 µM total dNTP (200 µM of each dATP, dTTP, dCTP, dGTP)
50 mM KCl
10 mM Tris-HCl, pH 8.3
1 mM MgCl₂,
0.05 units/µl AmpliTaq Gold ™ DNA polymerase*
```

*developed and manufactured by Hoffmann-La Roche and commercially available from PE Biosystems (Foster City, CA).

Amplification is carried out in a GeneAmp® PCR System 9600 thermal cycler (PE Biosystems, Foster City, Calif.), using the specific temperature cycling profile shown below.

| Pre-reaction incubation: | 94° C. for 12.5 minutes |
|---|---|
| 37 cycles: | |
| denature: | 95° C. for 45 seconds |
| anneal: | 60° C. for 30 seconds |
| extend: | 72° C. for 45 seconds |
| Final extension: | 72° C. for 7 minutes |
| Hold: | 10° C.–15° C. |

Detection Probes

Preferred probes used to identify the allelic sequence variants present in the amplified TCF-1 nucleic acid are described below. The probes are shown in the 5' to 3' orientation.

```
C-Allele Probe:
KW196 (SEQ ID NO:8) ATTACCCACCCCCCTCGGGA
A-Allele Probe:
KW118 (SEQ ID NO:9) CCGAGGTGGGTGGGTAAT
```

Probe Hybridization Assay, Immobilized Target Format

In the immobilized target format, a portion of the amplified nucleic acid is denatured, applied to a nylon filter, and immobilized as described below. The filter is then immersed in a solution containing labeled probe to allow hybridization to occur. Unbound probe is removed by washing under sequence-specific hybridization conditions, and the probes that remain bound to the immobilized nucleic acid are detected. The details of the assay are described below.

For use in the immobilized target detection format, described below, the probes are labeled with horseradish peroxidase (HRP) to facilitate detection. The synthesis of HRP-labeled oligonucleotides is described in Levenson and Chang, Chapter 13 in PCR Protocols, 1990, (Innis et al., eds., Academic Press, San Diego), incorporated herein by reference.

To denature the amplification products, 10 µl of amplification product are added to 90 µl of denaturation solution consisting of 4.5 µl of 0.5 M EDTA (pH 8.0), 7.2 µl of 5 N NaOH, and 78.3 µl of H2O. The mixture is incubated at room temperature for 10 minutes to complete denaturation.

Nylon filters (BioDyne™ B nylon filters, Pall Corp., Glen Cove, N.Y.) are prepared by soaking in H₂O for 5 to 10 minutes and further rinsing with 200 µl of H₂O. The 100 µl denatured sample mixture is applied under vacuum to the nylon membrane using a dot-blot manifold (Bio-Dot™ from Bio Rad, Richmond, Calif.). Each well is then rinsed with 200 µl of 0.4 N NaOH, then rinsed briefly with 2x SSC, and air dried until no pools of liquid are left. The immobilized DNA is crosslinked to the nylon filter by ultraviolet irradiation at a flux of 500 mJ/cm² using a Stratalinker™ (Stratagene, La Jolla, Calif.) UV light box (at the "autocrosslink" setting).

Hybridization is carried out in a hybridization buffer (5x SSPE, 0.5% SDS, where 20x SSPE is 3.6 M NaCl, 0.2 M NaH₂PO₄.H₂O, 20 mM EDTA, adjusted to pH 7.4 with NaOH) containing 2 !M HRP-labeled probe. The filters are allowed to hybridize for 25–30 minutes at 55° C. After hybridization, filters are rinsed in a wash buffer (2.5x SSPE, 0.1% SDS) at room temperature to remove most of the excess probe. A stringent wash is carried out in wash buffer for 12 minutes at 55° C. in a shaking water bath. The sequence-specific hybridization conditions of the stringent wash ensure that only probes exactly complementary to the target sequence remain bound.

HRP-labeled probes which remain bound to the immobilized amplification product are visualized as follows. A color development solution is prepared by mixing 100 ml of citrate buffer (0.1 M Sodium Citrate, pH 5.0), 5 ml 3,3',5, 5'-tetramethylbenzidine (TMB) solution (2 mg/ml TMB powder from Fluka, Milwaukee, Wis., dissolved in 100% EtOH), and 100 µl of 3% hydrogen peroxide. Filters first are rinsed in 100 mM sodium citrate (pH 5.0) for 5 minutes, then incubated in the color development solution with gentle agitation for 10 minutes at room temperature in the dark. The TMB, initially colorless, is converted by the probe-bound HRP in the presence of hydrogen peroxide into a colored precipitate. The developed filters are rinsed in water for several minutes and immediately photographed.

Probe Hybridization Assay, Immobilized Probe Format

In the immobilized probe format, the probes are immobilized to a solid support prior to being used in the hybridization. The probe-support complex is immersed in a solution containing denatured amplified nucleic acid to allow hybridization to occur. Unbound nucleic acid is removed by washing under sequence-specific hybridization conditions, and nucleic acid remaining bound to the immobilized probes is detected. The detection is carried out using the same chromogenic reaction used in the dot-blot assay described above. The details of the assay are described below.

For use in the immobilized probe detection format, described below, a moiety is attached to the 5' phosphate of the probe to facilitate immobilization on a solid support. Preferably, Bovine Serum Albumen (BSA) is attached to the 5' phosphate essentially as described by Tung et al., 1991, *Bioconjugate Chem.* 2:464–465, incorporated herein by reference. Alternatively, a poly-T tail is added to the 5' end as described in U.S. Pat. No. 5,451,512, incorporated herein by reference.

The probes are applied in a linear format to sheets of nylon membrane using a Linear Striper and Multispense2000™ controller (IVEK, N. Springfield, Vt.). Probe titers, 2 µM of KW196 (SEQ ID NO: 8) and 1.75 µM KW118 (SEQ ID NO: 9), are chosen to achieve signal balance between the allelic variants. Each sheet is cut to strips between 0.35 and 0.5 cm in width. To denature the amplification products, 20 µl of amplification product (based on a 50 µl reaction) are added to 20 µl of denaturation solution (1.6% NaOH) and incubated at room temperature for 10 minutes to complete denaturation.

The denatured amplification product (40 µl) is added to the well of a typing tray containing 3 ml of hybridization buffer (4x SSPE, 0.5% SDS) and the membrane strip. Hybridizations is allowed to proceed for 15 minutes at 55° C. in a rotating water bath. Following hybridization, the hybridization solution is aspirated, the strip is rinsed in 3 ml warm wash buffer (2× SSPE, 0.5% SDS) by gently rocking strips back and forth, and the wash buffer is aspirated. Following rinsing, the strips are incubated in 3 ml enzyme conjugate solution (3.3 ml hybridization buffer and 12 μL of strepavidin-horseradish peroxidase (SA-HRP)) in the rotating water bath for 5 minutes at 55° C. Then the strips are rinsed with wash buffer, as above, incubated in wash buffer at 55° for 12 minutes (stringent wash), and finally rinsed with wash buffer again.

Target nucleic acid, now HRP-labeled, which remains bound to the immobilized amplification product are visualized as follows. The strips first are rinsed in 0.1 M sodium citrate (pH 5.0) for 5 minutes, then incubated in the color development solution (described above) with gentle agitation for 8 to 10 minutes at room temperature in the dark. The TMB, initially colorless, is converted by the target-bound HRP, in the presence of hydrogen peroxide, into a colored precipitate. The developed strips are rinsed in water for several minutes and immediately photographed.

EXAMPLE 3

Presence of the A allele

Samples from individuals from 4 different populations were screened for the presence of the A allele. The sampled populations consisted of 47 African Americans, 47 U.S. Caucasians, 47 U.S. Hispanics, and 47 Japanese.

Genotyping was carried out using the allele-specific amplification methods essentially as described in Example 1, above. The protocol described in Example 1 represents an improved version of the assay actually used. The improvements made relate to the amplification and detection efficiency, but would not alter the qualitative results of the assay.

The results identified 19 out the 188 samples as containing the A allele: 2 African Americans, 11 U.S. Caucasians, 6 U.S. Hispanics, and 0 Japanese.

EXAMPLE 4

Frequency of the A Allele in Philippine Samples

Samples from 200 individuals from the Philippines were genotyped using the probe-based methods described in Example 2 (immobilized probe format). All individuals from this population were found to be homozygous for the C allele.

The absence of the A allele in this population may help explain why the occurrence of type 1 diabetes is lower in the Philippines than in the Caucasian population.

EXAMPLE 5

Association with Type 1 Diabetes

TCF-1 genotyping was carried out on individuals from 282 Caucasian families ascertained because they contained two offspring affected with type 1 diabetes. The TCF-1 genotypes of all individuals were determined. TCF-1 genotyping was carried out using the allele-specific amplification-based genotyping methods described in Example 1. In addition to the 564 offspring (2 sibs in each of 282 families) in the affected sib pairs on which ascertainment was based, there were 26 other affected children. There were 270 unaffected offspring among these families. The family-based samples were provided as purified genomic DNA from the Human Biological Data Interchange (HBDI), which is a repository for cell lines from families affected with type 1 diabetes. All of the HBDI families used in this study are nuclear families with unaffected parents and at least two affected siblings. These samples are described further in Noble et al., 1996, Am. J. Hum. Genet. 59:1134–1148, incorporated herein by reference.

It is known that the HLA genotype can have a significant effect, either increased or decreased depending on the genotype, on the risk for type 1 diabetes. In particular, individuals with the HLA DR genotype DR3-DQB1*0201/DR4-DQB1*0302 (referred to as DR3/DR4 below) appear to be at the highest risk for type 1 diabetes (see Noble et al., 1996, Am. J. Hum. Genet. 59:1134–1148, incorporated herein by reference). These high-risk individuals have about a 1 in 15 chance of being affected with type 1 diabetes. Because of the strong effect of this genotype on the likelihood of type 1 diabetes, the presence of the DR3-DQB1*0201/DR4-DQB1*0302 genotype could mask the contribution from the TCF-1 allelic variants.

Individuals within these families also were genotyped at the HLA DRB1 and DQB1 loci. Of the affected sib pairs, both sibs have the DR3/DR4 genotype in 90 families. Neither affected sib has the DR 3/4 genotype in 144 families. Exactly one of the affected pair has the DR 3/4 genotype in the remaining 48 families.

Statistical Methods

A number of statistical tests of association were carried out, as described in the following sections. Members of the same family are not independent observations, especially if the alternative hypothesis of genetic effect is true. Therefore, bootstrap methods were used throughout the analysis to assess significance. A standard non-parametric resampling of the families, which are the primary sampling units, was done using routines in the software package SPlus (MathSoft, Cambrige, Mass.). For each statistic, 1000 bootstrap samples were done. The confidence intervals were based on the simplest percentile method. The p-values were determined by finding the widest confidence interval that excludes the value of the parameter under the null hypothesis. If 1-α is the confidence level of that interval, the corresponding two-sided p-value is cc. For example, a 90% confidence interval corresponds to a p-value of 0.10.

Parents

The genotypes, allele frequencies, and genotype frequencies of the parents for each of the 282 families are shown in the tables below:

| Genotype Frequencies among Parent Pairs | |
|---|---|
| Genotypes | Number of Families |
| CC,CC | 170 |
| AC,CC | 90 |
| AA,CC | 8 |
| AC,AC | 14 |
| AC,AA | 0 |
| AA,AA | 0 |

The allele frequencies were calculated based on the number of A and C alleles out of the 1128 parental alleles (2 parents in each of 282 families, 2 alleles in each parent).

Allele Frequencies among Parents

| Allele | Number of Alleles | Frequency |
| --- | --- | --- |
| A | 134 | 0.119 |
| C | 994 | 0.881 |

The genotype frequencies within the parents were compared to the genotype frequencies expected assuming Hardy-Weinberg equilibrium (HWB). The data clearly fit the expected frequencies.

Genotype Frequencies among Parents

| Genotype | Expected | Observed |
| --- | --- | --- |
| CC | 0.776 | 0.777 |
| AC | 0.210 | 0.209 |
| AA | 0.014 | 0.014 |

Hardy-Weinberg Equilibrium (HWE)

HWE was tested also by looking at the table of transmitted by untransmitted alleles, shown below, and testing for independence of the rows and columns. All parents were included in this analysis, including the homozygous parents who are not informative in a TDT analysis (described below). Only the affected children are used.

Data for test of HWE at TCF-1 locus

| Observed Transmitted | Untransmitted A | C | Expected Transmitted | Untransmitted A | C |
| --- | --- | --- | --- | --- | --- |
| A | 16 | 140 | A | 17 | 139 |
| C | 113 | 911 | C | 112 | 912 |

Let $P_{AT}$ and $P_{AU}$ be the probability the A allele is transmitted and not transmitted, respectively. Define analogous terms for the C allele. The odds ratio $$(P_{AT}P_{CU})/(P_{AU}P_{CT})$$

measures the dependence of the transmitted and untransmitted alleles.

As can be seen the counts are very near the expected null values. This supports HWE at the TCF-1 locus. A p-value, which assumes independence of children from the same family, is 0.88. In this case, the bootstrap analysis to correctly account for the dependence of children was not done. The bootstrap should, in this case, reduce the level of significance even further.

Association Between TCF-1 and DRB1

A test for association in the general population between the DRB 1 locus and TCF-1 was carried out. Association would indicate the presence of population stratification related to these loci, which might affect the rest of the analysis. In addition, association cannot be maintained under unlinked loci for more than a single generation if the population is mating randomly. In that case, an association between the two loci could be maintained only if there were continuing selective pressures for or against a particular DRB1-TCF-1 combination.

The association was tested as follows. The haplotype not transmitted to each affected individual was observed. These untransmitted haplotypes can be viewed as a random sample from the population (under HWE). Let A and C indicate the two TCF-1 alleles. Let 3,4 and X indicate the serological group at DRB1, where X is any serological group other than the first two. Let AX be the probability of haplotype A and X. Let $N_{AX}$ be the number of such haplotypes. Define similar quantities for the other haplotypes. The odds of A given X can be estimated by $(N_{AX}/N_{CX})$. The odds ratio, (A3/C3)1 (AX/CX), can be estimated by $(N_{A3}N_{CX})/(N_{C3}N_{AX})$. Similar estimates apply to 4 vs. X and 4 vs. 3. If there were no association between the two loci, all three odds ratios would equal one.

The data are presented in the table, below. In the table, the odds ratio of A given 3 versus A given X is abbreviated 3 vs. X; analogous abbreviations are used for the other ratios. The significance of the odds ratio were estimated using a bootstrap analysis. The analysis showed no association between TCF-1 and DRB1. This means any association between the two loci in the transmission disequilibrium test (TDT) analysis is due to an interaction between the two loci in their effect upon risk.

Odds Ratios: Test of Association of TCF-1 with DRB1

| Odds Ratio | Estimated | Confidence Intervals | | | p-value |
| --- | --- | --- | --- | --- | --- |
| | | 80% | 90% | 95% | |
| 3 vs. X | 0.71 | 0.29, 1.25 | 0.23, 1.50 | 0.17, 1.75 | 0.49 |
| 4 vs. X | 0.71 | 0.35, 1.24 | 0.26, 1.45 | 0.22, 1.67 | 0.42 |
| 4 vs. 3 | 1.01 | 0.42, 2.49 | 0.33, 3.45 | 0.27, 4.22 | 1.00 |

This approach is not valid for the unaffected siblings of individuals ascertained for their affected status. The unaffected siblings are likely not to have gotten the same haplotype as their affected sibling. Therefore, the haplotypes not transmitted to the unaffecteds are more likely to contain high-risk haplotypes than the general population. The converse is not true for the affected children because the unaffected siblings are not considered in the ascertainment scheme. For affected siblings, there might be some tendency for false departures from non-association to appear because each child's ascertainment also depends on his or her sibling's disease status. This effect would lead to false positives and is not apparent here.

Gender Effects

The TCF-1 genotype distribution in the mothers, fathers, and offspring is shown in the table, below.

| | AA | AC | CC |
| --- | --- | --- | --- |
| Mothers | 6 | 67 | 209 |
| Fathers | 2 | 51 | 229 |
| Children | 13 | 197 | 650 |

In the absence of a gender-related effect, one would expect the mothers and fathers to have the same distribution. The chi-squared statistic for the same distribution in the mothers as in the fathers is 5.08 with a p-value of 0.08. As the first column has few data, a chi-squared test also was run on the second and third columns only. This had a statistic of 2.71 with a p-value of 0.10. This suggests either that there are more A alleles present in the mothers than in the fathers or that the risk of A is greater if that allele is received from the mother. The ascertainment scheme would then increase the number of mothers carrying A in the sample.

Under HWE, this effect can also be analyzed by looking at alleles not transmitted to affected children. The odds ratio for the type of untransmitted alleles relative to maternal or paternal origin is (Am·Cp)/(Cm·Ap), where Am is the number of untransmitted A alleles of maternal origin, Ap is the number of untransmitted A alleles of paternal origin, and other notation for the C allele is defined analogously. This odds ratio measures the population-wide relative frequency of A in women.

Odds Ratios (OR): Test of Association of Allele A with Maternal Origin

| Group | N | OR | Confidence Intervals | | | p-value |
|---|---|---|---|---|---|---|
| | | | 80% | 90% | 95% | |
| Total | 1180 | 1.94 | 1.45, 2.65 | 1.31, 2.94 | 1.20, 3.25 | 0.01 |
| DR3/DR4 | 474 | 1.62 | 1.08, 2.46 | 0.95, 2.85 | 0.86, 3.29 | 0.14 |
| Non-DR3/DR4 | 706 | 2.19 | 1.47, 3.33 | 1.34, 3.80 | 1.27, 4.22 | 0.01 |

The fact that the odds ratio is greater than one indicates that women carry the A allele more often than do men. This effect appears more strongly in the mothers of non-DR3/DR4 children, who are presumably less likely on average to carry a DRB 13 or 4 allele. There is a slight bias in this test because there are at least two affected children in each family. As shown later, risk appears to be attributable to paternal origin which should make men in the sample more likely to carry the A allele, contrary to this result.

Odds ratios for maternal versus paternal origin of transmitted A alleles also were calculated from allele transmissions from heterozygous parents, as shown in the tables, below. The transmissions to affected and unaffected offspring were calculated separately.

Odds Ratios (OR): Test of Association of Allele A with Maternal Origin Transmission from Heterozygous Parents to Affected Offspring

| Group | N | OR | Confidence Intervals | | | p-value |
|---|---|---|---|---|---|---|
| | | | 80% | 90% | 95% | |
| Total | 253 | 0.61 | 0.45, 0.81 | 0.40, 0.88 | 0.38, 0.92 | 0.01 |
| DR3/DR4 | 104 | 0.50 | 0.31, 0.73 | 0.26, 0.80 | 0.24, 0.88 | 0.01 |
| Non-DR3/DR4 | 149 | 0.67 | 0.44, 1.04 | 0.39, 1.15 | 0.34, 1.24 | 0.25 |

Odds Ratios (OR): Test of Association of Allele A with Maternal Origin Transmission from Heterozygous Parents to Unaffected Offspring

| Group | N | OR | Confidence Intervals | | | p-value |
|---|---|---|---|---|---|---|
| | | | 80% | 90% | 95% | |
| Total | 99 | 1.23 | 0.73, 2.05 | 0.62, 2.39 | 0.56, 2.86 | 0.63 |
| DR3/DR4 | 19 | 0.78 | 0.13, 2.88 | 0.02, 4.67 | 0.00, 9.00 | 0.81 |
| Non-DR3/DR4 | 80 | 1.36 | 0.77, 2.36 | 0.67, 2.75 | 0.58, 3.25 | 0.48 |

The odds ratio calculated from the transmissions from heterozygous parents to affected offspring are less than one, which indicates that heterozygous men transmit A more frequently than heterozygous women. As this is based only on heterozygous parents, this effect cannot be due to differences in the genotype distributions of males and females. There appears to be little difference in this effect between DR3/DR4s and non-DR3/DR4s, but there is not enough evidence to be sure. There is no visible difference in transmission among the unaffecteds, but there are few data.

TCF-1 Allele Transmission

One method of detecting allelic effects is by analyzing the allele transmission rates. If the alleles are not associated with the disease state, then it would be expected that the A and C alleles would be transmitted, for example, from a heterozygous parent to an affected offspring in a 50:50 ratio. Deviations in the transmission rates indicate an association of an allele with the disease state.

A number of statistical tests have been proposed for analyzing deviations in allele transmission rates. For example, a transmission disequilibrium test (TDT) is described in Spielman et al., 1993, Am. J. Hum. Genet. 52:506–516; Ewens and Spielman, 1995, Am. J. Hum. Genet. 57:455–464; and Ewens and Spielman, 1999, Supplement 20 in Current Protocols in Human Genetics (Dracopoli et al., eds., 1984 with quarterly updates, John Wiley & Sons, Inc.), each incorporated herein by reference. In particular, Speilman et al., 1993, discussed the statistical properties of the TDT applied to families containing two affected offspring.

In the present case, an analysis was carried out based on the ratio of A allele to C allele transmissions. This ratio, A/C, provides a measure of relative risk, albeit somewhat distorted by the ascertainment of affected pairs with unaffected parents. A bootstrap analysis was used to assess significance. The use of the ratio of transmissions is equivalent to an analysis based on the proportion of A transmissions because there is a one-to-one correspondence between A/C and A/(A+C).

In the first case, the relative risks were calculated for subgroups defined by the disease status of the offspring, the HLA genotype of the offspring, and the maternal/paternal origin of the transmitted allele. Abbreviations used in the table, below, are: af=affected offspring; un=unaffected offspring; 34=DR3/DR4 offspring genotype; n34=non-DR3/DR4 offspring genotype; m=maternal origin; and p=paternal origin.

Relative Risk (RR) calculated from TDT

| Group | N | RR | Confidence Intervals | | | p-value |
|---|---|---|---|---|---|---|
| | | | 80% | 90% | 95% | |
| af, 34, m | 52 | 0.76 | 0.53, 1.08 | 0.46, 1.17 | 0.42, 1.28 | 0.38 |
| af, 34, p | 52 | 1.54 | 1.19, 2.04 | 1.10, 2.20 | 1.04, 2.45 | 0.05 |
| af, n34, m | 90 | 1.17 | 0.87, 1.54 | 0.81, 1.71 | 0.77, 1.94 | 0.46 |
| af, n34, p | 59 | 1.74 | 1.26, 2.55 | 1.15, 2.83 | 1.07, 3.11 | 0.02 |
| un, 34, m | 11 | 1.00 | 0.50, 2.20 | 0.40, 3.00 | 0.33, 4.00 | 1.00 |
| un, 34, p | 8 | 1.29 | 0.50, 5.00 | 0.33, 9.00 | 0.25, ∞ | 0.87 |
| un, n34, m | 58 | 1.64 | 1.12, 2.42 | 1.00, 2.70 | 0.93, 3.14 | 0.11 |
| un, n34, p | 22 | 1.20 | 0.74, 1.94 | 0.67, 2.27 | 0.60, 2.54 | 0.76 |

The only clearly significant results are for fathers of affected DR3/DR4s and non-DR3/DR4s. The result for the mothers of unaffected non-DR3/DR4s is mildly suggestive.

The relative risks also were calculated based on subgroups defined by combinations of the above categories, as shown in the table, below.

Relative Risk (RR) calculated from TDT (grouped data)

| Group | N | RR | Confidence Intervals | | | p-value |
| --- | --- | --- | --- | --- | --- | --- |
| | | | 80% | 90% | 95% | |
| af, 34 | 104 | 1.08 | 0.86, 1.35 | 0.81, 1.44 | 0.75, 1.54 | 0.76 |
| af, n34 | 149 | 1.37 | 1.10, 1.71 | 1.03, 1.85 | 1.00, 1.96 | 0.08 |
| un, 34 | 19 | 1.11 | 0.64, 2.17 | 0.53, 2.75 | 0.43, 3.50 | 0.96 |
| un, n34 | 80 | 1.50 | 1.08, 2.09 | 1.00, 2.29 | 0.92, 2.45 | 0.11 |
| af, m | 142 | 1.00 | 0.81, 1.24 | 0.77, 1.31 | 0.74, 1.39 | 1.00 |
| af, p | 111 | 1.64 | 1.34, 2.08 | 1.26, 2.24 | 1.22, 2.37 | <0.001 |
| un, m | 69 | 1.51 | 1.07, 2.14 | 0.97, 2.37 | 0.88, 2.64 | 0.15 |
| un, p | 30 | 1.22 | 0.80, 1.89 | 0.71, 2.16 | 0.63, 2.43 | 0.64 |
| 34, m | 63 | 0.80 | 0.58, 1.08 | 0.52, 1.16 | 0.48, 1.25 | 0.40 |
| n34, m | 60 | 1.33 | 1.02, 1.73 | 0.95, 1.91 | 0.90, 2.10 | 0.18 |
| 34, p | 148 | 1.50 | 1.13, 2.03 | 1.00, 2.23 | 0.94, 2.37 | 0.11 |
| n34, p | 81 | 1.57 | 1.19, 2.16 | 1.09, 2.35 | 1.00, 2.56 | 0.06 |
| af | 253 | 1.24 | 1.06, 1.46 | 1.02, 1.52 | 0.98, 1.59 | 0.08 |
| un | 99 | 1.41 | 1.06, 1.87 | 0.98, 2.06 | 0.91, 2.21 | 0.13 |
| 34 | 123 | 1.08 | 0.87, 1.36 | 0.81, 1.46 | 0.75, 1.53 | 0.66 |
| n34 | 229 | 1.41 | 1.15, 1.72 | 1.10, 1.87 | 1.04, 2.00 | 0.03 |
| m | 211 | 1.14 | 0.95, 1.38 | 0.89, 1.45 | 0.85, 1.54 | 0.40 |
| p | 141 | 1.54 | 1.27, 1.89 | 1.20, 2.05 | 1.12, 2.15 | 0.005 |
| Total | 352 | 1.29 | 1.12, 1.49 | 1.07, 1.57 | 1.03, 1.62 | 0.03 |

The increased A allele transmission from the fathers to affected offspring is highly significant. There is also marginal significance for other groups that include some of the fathers of affecteds. For the fathers of affecteds, the relative risk is estimated to be 1.64. This represents the risk of being one of a pair of affected sibs. Also, note that the numbers include the extra affected children.

Transmission among the affected, among the non-DR3/DR4s and from the fathers all range from somewhat to very significant. Transmission from fathers has the most significant result. It appears that the increased transmission may be isolated to the fathers of affecteds only. The slight elevation of A transmitted to the unaffecteds could be due to chance.

Partitioning Risk

The following analysis was carried out to partition the effects of linkage and the effects of association in order to determine whether the TCF-1 locus is causally related to type 1 diabetes or is in linkage disequilibrium with some other causally related locus. The analysis is based on the 51 heterozygous fathers and the corresponding affected sib pairs. Extra affected offspring were not included.

Let AA, AC, and CC represent the frequencies with which the heterozygous fathers transmit an A allele to both sibs, an A allele to one sib and a C allele to the other sib, or a C allele to both sibs, respectively. If there is no genetic effect, the expected transmission frequencies are 0.25 AA, 0.5 AC, and 0.25 CC. The observed transmission frequencies were 19.25 AA, 25 AC and 6.75 CC. The observed numbers are not all integers because, where the parental genotype did not allow unambiguous determination of which parent transmitted which allele, a decimal transmission frequency was assigned based on the probability of the event. For example, a family in which both sibs received an A allele from the father or, with equal probability, one sib received an A allele from the father and one from the mother, would contribute 0.5 to the calculated frequency with which the heterozygous fathers transmit an A allele to both sibs, AA.

Consider the following ratios that measure genetic effect:

$$AA|CC,\ AC|CC,\ AC|AA,\ \frac{(AA \cdot CC)}{(AC \cdot AC)},\ \text{and}\ \frac{(AA+CC)}{AC}$$

AA/CC is a measure of the relative risk of the A allele, whether caused by the TCF-1 locus or a locus in linkage disequilibrium with TCF-1. AC/CC is a measure of the relative risk of sibs with A alleles who do not share alleles with their affected sibling compared to sibs with C alleles who do. $(AA \cdot CC)/AC^2$ is a measure of the relative risk due to linkage once the TCF-1 allele is known. These latter two ratios provide insight as to whether TCF-1 is the causal locus. (AA+CC)/AC is a measure of the relative risk of sibs having alleles identical by descent (IBD) compared to non-IBD.

Let p be the risk associated with allele A and r be the risk associated with allele C. These risks might be due to the allele itself or to linkage disequilibrium with a causative allele at a linked locus. Let s be the added risk to the sib pair due to their sharing alleles at TCF-1 given that the TCF-1 genotype is already known. Let t be the added risk to the pairs who do not share alleles. Given the transmitted alleles, the risk to the AA pairs is $p^2s$, to the AC pairs is prt, and to the CC pairs is $r^2s$.

Several ratios, shown in the table below, that measure genetic effect were used to test the relative values of various risks. The expected values of the ratios, also given in the table below, can be calculated in terms of the above values for the risks of AA pairs, AC pairs, and CC pairs. Limits on the outcomes of these statistics can be predicted under various hypotheses, shown in the table below. Where predictable, the limits for these statistics are shown in the succeeding table.

| Hypothesis | Assumptions |
| --- | --- |
| Null | No genetic effect |
| A | Only TCF-1 is causally related. (assumes A to be associated with higher risk.) |
| B | TCF-1 is not causally related. TCF-1 is linked to another causally related locus, but with no linkage disequilibrium |
| C | TCF-1 is not causally related. TCF-1 is linked to another causally related locus and in linkage disequilibrium. (assumes A to be associated with higher risk.) |
| D | TCF-1 is causally related. TCF-1 is linked to another causally related locus, but with no linkage disequilibrium. |
| E | TCF-1 is causally related. TCF-1 is linked to another causally related locus and in linkage disequilibrium. |

Predicted Outcomes

| Hypothesis | AA/CC | AC/CC | AC/AA | $\frac{(AA \cdot CC)}{(AC \cdot AC)}$ | $\frac{(AA + CC)}{AC}$ |
| --- | --- | --- | --- | --- | --- |
| Expected | $p^2/r^2$ | 2pt/rs | 2rt/ps | $s^2/4t^2$ | $(p^2s + r^2t)/2prt$ |
| Null | 1 | 2 | 2 | ¼ | 1 |
| A | >1 | >2 | <2 | ¼ | >1 |
| B | 1 | <2 | <2 | >¼ | >1 |
| C | >1 | ? | ? | >¼ | >1 |
| D | >1 | ? | ? | >¼ | >1 |
| E | ? | ? | ? | ? | >1 |

When there are two causal loci (hypotheses D and E), the direction of the alternative depends on the relative risks of the two loci, the degree of linkage, and the degree and direction of linkage disequilibrium between the loci.

Below are the results calculated from the TCF-1 data.

Partition of Risk to Affected Sib Pairs from Heterozygous Fathers

| Partition of Risk to Affected Sib Pairs from Heterozygous Fathers | | | | |
|---|---|---|---|---|
| | | Confidence Intervals | | |
| N=51 | 80% | 90% | 95% | p-value |
| AA/CC | 2.85 1.81, 5.25 | 1.57, 6.20 | 1.39, 8.00 | 0.01 |
| AC/CC | 3.70 2.37, 6.82 | 2.05, 8.35 | 1.81, 10.36 | 0.10 |
| AC/AA | 1.30 0.92, 1.82 | 0.84, 2.06 | 0.78, 2.24 | 0.13 |
| (AA·CC) (AC·AC) | 0.21 0.09, 0.40 | 0.70, 0.49 | 0.06, 0.59 | 0.61 |
| (AA+CC) AC | 1.04 0.75, 1.43 | 0.68, 1.58 | 0.64, 1.70 | 0.99 |

AA/CC is higher than expected under the null hypothesis, which shows a definite association of risk with the A allele, whether through the TCF-1 locus or a locus in linkage disequilibrium with TCF-1. AC/CC is higher than expected under the null hypothesis, which shows that sibs with A alleles who do not share alleles with their affected sibling are at greater risk than sibs with C alleles who do. This suggests that TCF-1 is indeed a causative locus. AC/AA is lower than expected under the null hypothesis, consistent with the previous results showing that an identical by descent (IBD) A is at greater risk than a non-IBD C. $(AA \cdot CC)/AC^2$ is slightly below its expected value under the null hypothesis, which shows that there is no added risk due to linkage once the TCF-1 allele is known. These results are consistent with there being no other linked causative locus, whether in addition to, or instead of, TCF-1. (AA+CC)/AC measures the risk of IBD status vs. non-IBD status. It is slightly higher than expected under the null hypothesis, but consistent with the null hypothesis.

The values of (AA+CC)/AC and AA/CC can be solved to find estimates of the relative risk of A to C, which is p/r. Let S be the value of the statistic (AA+CC)/AC. Then, the estimate of p/r is $(s \pm \sqrt{s^{21}})r$. Let T be the observed value of AA/CC. Then, another estimate of p/r is $\sqrt{T}$.

The estimate of the relative risk of the A allele to the C allele based on S is 1.33; the estimate based on T is 1.69. Both estimate suggests a modest increased risk associated with the A allele. The upper end of the 80, 90, and 95% confidence intervals for p/r derived from S are 2.45, 2.80 and 3.70. The lower ends cannot be evaluated, but the intervals include 1. Confidence intervals for p/r based on T can be found by taking the square root of the intervals given in the table for AA/CC. The upper ends are fairly consistent with the S-based intervals, but the lower ends do not include the null value of 1. The confidence intervals include the possibility, but not the probability, that the relative risk may be nearly as great as 3.

Conclusions

Based on the above analysis, the following conclusions were drawn.

1. Distribution of TCF-1 in the general population.
   (a) There is no evidence of Hardy-Weinberg disequilibrium at the TCF-1 locus.
   (b) There is no evidence of association between TCF-1 and the DRB1 03, 04, and X serologic groups.
   (c) Women appear to carry allele A more frequently than men.

2. Risk of type 1 diabetes associated with TCF-1.
   (a) Overall, heterozygous parents transmit allele A to their affected children more frequently than allele C, which indicates an association of the A allele with the disease state.
   (b) The increased transmission of the A allele to the unaffected siblings of affected children is not statistically significant and is most likely due to chance.
   (c) Heterozygous men transmit allele A to their affected children more frequently than they transmit allele C, probably without respect to the DRB 1 3/4 status of the child, which indicates an association of an A allele of parental origin with the disease state.
   (d) Heterozygous women transmit both alleles at equal rates to their affected children.
   (e) Based on limited evidence, the heterozygous fathers and mothers of affected children transmit both alleles at equal rates to their unaffected offspring.

3. Risk from TCF-1 vs. risk from other neighboring loci.
   (a) Heterozygous fathers transmit allele A to both members of the affected sib pair more frequently than they transmit allele C, confirming increased risk associated with allele A.
   (b) Heterozygous fathers of an affected sib pair transmit both alleles, i.e., one A and one C, more than twice as often as they transmit two copies of allele C, which is more often than would be due to chance. This suggests that there is more risk from receiving allele A than from receiving the same allele as your affected sibling, favoring TCF-1 as the risk-inducing locus.
   (c) Heterozygous fathers of an affected sib pair transmit both alleles less than twice as often as they transmit two copies of allele A, which is less often than would be due to chance and is consistent with results 3.a and 3.b.
   (d) There is no added risk due to identity by descent with an affected sibling beyond that contributed by allele A, consistent with their being no other risk-related loci linked to TCF.
   (e) The relative risk due to receiving an A allele instead of a C allele from one's father was estimated using two different measures to be 1.33 and 1.69, respectively. Precisely, the risk measured is the risk of being affected by type 1 diabetes and simultaneously having a sibling with type 1 diabetes. Confidence intervals suggest that the data are compatible with values of relative risk ranging from 1.2 to nearly 3.

Overall, the data are most consistent with moderate increased risk for type 1 diabetes to children who receive a TCF-1 A allele from their fathers. This increased risk is probably not dependent on DRB1 3/4 status. There appears to be no added risk when the A allele is received from one's mother. The data indicate that there are no other risk-related loci linked to TCF-1. Women in the general population appear to have a greater frequency of the TCF-1 A allele than men.

All samples were subsequently retyped using the reverse line-blot methods described in Example 2. With the exception of one sample, both protocols yielded the consistent genotypes. The one discrepant result is believed to result from a sample mix-up, rather than an actual typing error. During this further analysis, it was discovered that a small number of the originally determined genotypes, although correct, were recorded in a computer database incorrectly. The statistical analysis described above was carried out using the data as entered. It is clear that the data entry errors were so few that the statistical conclusions remain valid.

EXAMPLE 6

Association with Type 1 Diabetes in Mexican American Families (Preliminary Results)

Sixty-three Mexican American families that contain offspring affected with type 1 diabetes were analyzed essentially as described in the previous example. All TCF-1 genotyping was carried out using the allele-specific amplification-based genotyping methods described in Example 1. As the sample size is significantly smaller, these results must be considered as preliminary.

| Parent genotypes | |
|---|---|
| Genotypes of Parents | Number of Families |
| AA,CC | 1 |
| AC,AC | 1 |
| AC,CC | 21 |
| CC,CC | 40 |
| AA,AC | 0 |
| AA,AA | 0 |

| TCF-1 allele frequencies in parents: | | |
|---|---|---|
| Allele | Number | Frequency |
| A | 25 | 0.099 |
| C | 227 | 0.900 |

Transmission rates were determined from the genotypes of 21 affected offspring of AC,CC parents. The expected and observed genotypes are shown below, along with the calculated transmission rates. The frequency of the AC genotype provides the transmission rate of the A allele, and the frequency of the CC genotype provides the transmission rate of the C allele.

| Genotype | Expected | Observed | Frequency |
|---|---|---|---|
| AC | 11.5 | 7 | 33.3% |
| CC | 11.5 | 14 | 66.7% |

The above results, although not statistically significant, may suggest a trend that is opposite to the trend observed in the larger study presented in the previous example. It is possible that this reflects a difference in the populations studied. However, given the small number of affected sibs genotyped (21 total), it is more likely that the results are a statistical artifact.

The results in the previous example indicate that the effect of the TCF-1 genotype is small, and it may require large study populations to unambiguously determine the effect. Furthermore, the effect may be masked by the more significant effects of the HLA genotype. The present study was not large enough to permit stratification by HLA genotype, as was done in the previous example. Verification of the suggested trend would be expected to require a significantly larger study population.

EXAMPLE 7

Association with Multiple Sclerosis

TCF-1 genotyping was carried out on individuals from two groups of families ascertained because they contained a single offspring affected with multiple sclerosis (MS). The first group consisted of 180 families, mostly caucasian, but containing families of other ethnicity. The second group consisted of 74 Spanish families. TCF-1 genotyping of the affected child and both unaffected parents was carried out using the probe-based genotyping methods described in Example 2. The distribution of parental genotypes and the frequencies of the A allele, f(A), are shown in the table, below.

| Genotypes of Parents | Group 1 (N = 180) | Group 2 (N=74) |
|---|---|---|
| CC, CC | 111 | 47 |
| CC, AC | 50 | 20 |
| CC, AA | 5 | 3 |
| AC, AC | 11 | 4 |
| AC, AA | 3 | 0 |
| | f(A)=0.1264 | f(A)=0.1148 |

TCF-1 Allele Transmission: Group 1

The allele transmission rates were analyzed by considering only informative families, i.e., families in which there is at least one heterozygous parent. Within Group 1, 53 of the families contain one heterozygous and one homozygous parent. In these families, the number of A alleles transmitted, out of the 53 informative alleles transmitted from the heterozygous parent, were counted; the 53 alleles transmitted from the homozygous parents were uninformative and not considered. In 11 families, both parents are heterozygous. In these families, the number of A alleles out of the 22 alleles transmitted from both parents to the 11 offspring were counted. In both cases, under the null hypothesis of no genetic effect, the A and C alleles would be transmitted with equal probability, yielding an expected 50:50 ratio. Deviations in the transmission rates indicate an association of an allele with the disease state. The significance of the deviations were analyzed using a chi-squared test. In addition, because under the null hypothesis, allele transmissions are binomially distributed with a probability of transmitting an A allele of 0.5, exact probability can be determined. The probability of a deviation in transmission rates at least as great as that observed, $$\text{Probability}\{|X-\mu| \geq |f(A)-\mu|\},$$

where f(A) is the observed frequency of A transmissions and $\mu$ is the expected value of f(A), was calculated, which corresponds to a standard two-sided test of the null hypothesis.

The allele transmission data from the 64 informative families from the 180 families of Group 1 are shown in the table below.

| | Allele Transmissions, Group 1 | | |
|---|---|---|---|
| Parental Genotypes | Number of Allele transmissions | Allele Transmitted A | C |
| 50 CC, AC | 50 | 31 | 19 |
| 11 AC, AC | 22 | 14 | 8 |
| 3 AC, AA | 3 | 2 | 1 |

Out of a total of 75 allele transmission events, the A allele was transmitted 47 times and the C allele was transmitted 28 times. The expected values of allele transmissions under the null hypothesis would be 37.5 for each allele. A chi-square test of the significance yielded a P-value of 0.028. The probability of observing a deviation in transmission rates at least as great as that observed, obtained directly from a binomial distribution, yielded a two-sided P-value of 0.037. The results indicate that increased transmission of A alleles to affected offspring is statistically significant.

Association with the HLA Genotype

It is known that the HLA DRB1*1501-DQB1*0602 haplotype (IDR15) is associated with increased susceptibility to MS (see, for example, Oksenberg et al., 1993, JAMA 270:2362–2369, incorporated herein by reference). In order to determine whether the alleles at these two loci, TCF-1 and HLA, interact to determine MS susceptibility, the HLA genotypes were determined and the data were stratified based on the HLA genotype of the offspring. Of the 64 offspring in the informative families, 33 were DR15 and 31 were not DR15.

The allele transmission data from the 33 informative families in which the offspring had the DR15 genotype, selected from the Group 1 families, are shown in the table below.

| Allele Transmissions to DR15 Offspring | | | |
|---|---|---|---|
| Parental | Number of Allele | Allele Transmitted | |
| Genotypes | transmissions | A | C |
| 24 CC, AC | 24 | 14 | 10 |
| 7 AC, AC | 14 | 9 | 5 |
| 2 AC, AA | 2 | 2 | 0 |

Of the 40 alleles transmitted to DR15 offspring, 25 were A alleles and 15 were C alleles. Under the null hypothesis of no genetic effect, the expected transmissions would be 20 of each.

The allele transmission data from the 31 informative families in which the offspring did not have the DR15 genotype, selected from the Group 1 families, are shown in the table below.

| Allele Transmissions to non-DR15 Offspring | | | |
|---|---|---|---|
| Parental | Number of Allele | Allele Transmitted | |
| Genotypes | transmissions | A | C |
| 26 CC, AC | 26 | 17 | 9 |
| 4 AC, AC | 8 | 5 | 3 |
| 1 AC, AA | 1 | 0 | 1 |

Of the 35 alleles transmitted to non-DR15 offspring, 22 were A alleles and 13 were C alleles. Under the null hypothesis of no genetic effect, the expected transmissions would be 17.5 of each.

In general, random variables W and Z are independent if the probability of W conditioned on the value of Z is equal to the probability of W (unconditional). Using the observed frequencies as estimates of probabilities, it is apparent that the effect of the A allele and the DR15 genotype are independent. In particular, the conditional frequency of transmission of the A allele, given the offspring is DR15 (25/40=0.625), is virtually identical to the unconditional frequency of transmission of the A allele (47/75=0.627). Similarly, the conditional frequency of transmission, given the offspring is not DR15 (22/35=0.629), is virtually identical to the unconditional frequency of transmission. These results indicate that the effects of the TCF-1 and DR15 genotypes are independent. This conclusion is supported by a chi-squared test of significance for the independence of TCF-1 and DR15 genotypes, which yields a P-value of 0.97 (see 2×2 tables, below).

| Test of Independence of TCF-1 and DR15 | | |
|---|---|---|
| Observed | A | C |
| DR15 | 25 | 15 |
| nonDR15 | 22 | 13 |
| Expected | A | C |
| DR15 | 25.07 | 14.93 |
| nonDR15 | 21.93 | 13.07 |

TCF-1 Allele Transmission: Groups 1 and 2

Group 2 consists of 74 informative MS simplex families of Spanish origin. These families were typed for TCF-1 only. The allele transmission data are shown in the table, below.

| Allele Transmissions, Group 2 | | | |
|---|---|---|---|
| Parental | Number of Allele | Allele Transmitted | |
| Genotypes | transmissions | A | C |
| 20 CC, AC | 20 | 12 | 8 |
| 4 AC, AC | 8 | 4 | 4 |
| 0 AC, AA | | | |

Because of the small numbers, the data were combined with the Group 1 data and the allele transmission rates were analyzed as described above. A combined total of 103 allele transmissions were observed, 28 from the Group 2 families and 75 from Group 1 families. Under the null hypothesis, the expected number of A and C alleles transmitted would be 51.5 each. In contrast, 63 A alleles were transmitted and 40 C alleles were transmitted. A chi-square test of the significance yielded a P-value of 0.023. The probability of observing a deviation in transmission rates at least as great as that observed, calculated from a binomial distribution, yielded a two-sided P-value of 0.030. The results are consistent with the data obtained solely from Group 1 and indicate a statistically significant association of the A allele with MS.

EXAMPLE 8

Association with Asthma and Atopy

This example describes the results of a study of the association between the TCF-1 genotype and asthma and atopy.

Asthma is an inflammatory disease of the airways of the lung, typically recognized by physician diagnosis. Associated with asthma is a non-specific bronchial hyper-responsiveness. Bronchial responsiveness typically is measured by the dose response of the airflow to a bronchoconstrictor, such as methacholine.

Atopy (often referred to interchangeably as allergy), caused by the immune reaction to allergens, is typified by the intensity of the IgE response to an allergen. Atopy typically is recognized clinically by skin prick tests, which indicate the presence of allergen-specific IgE, by the presence of allergen-specific IgE in the serum, by elevations of total serum IgE, or by the presence of eosinophilia in the blood.

Although asthma is often associated with atopy, asthma is unlikely to be a single disease. Most childhood asthmatics are also atopic. In contrast, adult-onset asthma is a poorly defined disease that often is not associated with atopy. Furthermore, atopic individuals differ in the allergens to which they react, and asthma and bronchial hyper-responsiveness are associated with allergy to house dust mite antigen, but not with grass pollens.

Asthma and atopy are known to have a genetic basis and are likely to be influenced by a few genes with moderate effects. Diseases such as asthma are likely to be due to allelic variants in genes that alter gene function in a subtle way, rather than eliminate function. However, the genetic basis remains to be elucidated.

Subjects

Two panels of families were studied. Panel A consisted of 447 British individuals from 66 nuclear and 5 extended pedigrees ascertained through family members with asthma or rhinitis. Panel B consisted of 401 Australian subjects from 88 nuclear families each with 2 or more atopic siblings identified from a random population sample. These panels are described in Moffat et al., 1994, Lancet 343:1597–1600, incorporated herein by reference. The population and traits measured are described also in Daniels et al., 1996, Nature 383(19):247–250, incorporated herein by reference.

Clinical Data

The variables analyzed are shown in the following table.

| Variable | Method of Determination |
| --- | --- |
| asthma | Based on standard ATS questionnaires |
| atopy | Determined by a positive skin tests to allergens, and/or positive specific serum IgE tests to common allergens, and/or elevations of the total IgE. This approximates a clinical definition of atopy. |
| wheeze | Bronchial hyper-responsiveness measured by the dose-response to methacholine |
| lige | total serum IgE level (log transformed) |
| dige | age- and sex-matched total serum IgE levels, divided into deciles (1 = lowest 10%, 2 between 10% and 20% and so on) |
| iger | IgE normalised and adjusted for age and sex by regression |
| psti | Skin test index: the sum of skin tests to house-dust mite and grass pollen |
| rasti | Radioabsorbance skin test index (Rast index): the sum of specific serum IgE titers to house-dust mite and grass pollen |
| wheeze* | Bronchial responsiveness to methacholine |
| lnslope* | Bronchial responsiveness measured as the log-transformed slope of the dose-response to methacholine |
| lneos* | Eosinophil counts (log transformed) |

*measured in the Australian population only:

The above variables all are positively correlated. In both groups, atopy, lige, dige, iger, psti and rasti are strongly positively correlated (lige dige and iger are related by definition). Correlations of these variables with asthma and wheeze are less strong. As noted above, asthma is a poorly defined disease which may have multiple etiologies, including disease not associated with the atopic state. This may account for the higher correlation with variables that measure the IgE level and are more directly related to the atopic state.

Genotyping

The genotype of each individual was determined essentially as described in Example 1, above, except that minor modifications of the reaction conditions were made to optimize the assay for use with a different thermal cycler. The differences between the assay described in Example 1 and the conditions actually used potentially could affect the amplification and detection efficiency, but likely would not alter the qualitative results of the assay.

Analysis

The data were analyzed in order to detect the presence of genetic effects, rather than the size of the effect. Absence of a genetic effect would indicate that neither the TCF-1 locus nor any linked locus directly affects any of the phenotypic variables or any other characteristics leading to the ascertainment of the family.

TDT (transmission disequilibrium test) methods, analogous to the methods described above for the analysis of the association of TCF-1 alleles with type 1 diabetes, were used. All informative allele transmissions from a heterozygous parent to a child, where valid genotypes were provided for all three members of a child-parent trio, were used for the TDT. It was assumed that, conditional on the pedigree structure and parental heterozygosity, the outcomes of these informative transmissions were more or less independent under the null hypothesis of no genetic effect. In general, the samples seemed large enough to use large-sample statistical results.

For the discrete variables; asthma, wheeze, and atopy; p-values were obtained from an exact test of proportions. For continuous variables, which include the various measures of IgE response, t-tests and Wilcoxon rank-sum tests were used to compare the values of the continuous variables for children who have received an A allele to the values for children who received a C allele. Only children with a heterozygous parent were included.

Results

1. British Data:

The British data contained 47 informative child-parent trios in 17 pedigrees. Of these, 3 had two heterozygous parents, 28 had a heterozygous father only and 16 had a heterozygous mother. The genotype distributions are shown below.

| | Genotype Distribution (British) | | | | |
| --- | --- | --- | --- | --- | --- |
| | CC (%) | AC (%) | AA (%) | NA* | total |
| men | 152 (80) | 39 (20) | 2 (1) | 40 | 233 |
| women | 149 (82) | 31 (17) | 2 (1) | 32 | 214 |
| total | 301 (80) | 70 (19) | 4 (1) | 72 | 447 |

* NA: genotype not available

These families exhibit no obvious differences in genotype distribution between men and women.

Discrete Variables

The allele transmissions from heterozygous parents to children categorized by disease state are shown in the table, below. Both the number (#) and proportion (%) are shown. The alleles transmitted from the fathers and mothers are reported separately. For the "all" category, children were scored as receiving an A allele if either heterozygous parent transmitted an A allele. This has the advantage of making each count independent as no two counts represent the same child. (Children with two heterozygous parents are not counted twice.) As a consequence, the number of alleles transmitted by fathers and mothers do not add up to the number in the "all" category.

| Transmissions from Heterozygote Parents (British) | | | | | | |
|---|---|---|---|---|---|---|
| | Fathers | | Mothers | | All | |
| | A # (%) | C # (%) | A # (%) | C # (%) | A # (%) | C # (%) |
| All children | 15.5 (50) | 15.5 (50) | 9.5 (50) | 9.5 (50) | 25 (53) | 22 (47) |
| Asthma | | | | | | |
| No | 5 (42) | 7 (58) | 3 (50) | 3 (50) | 8 (47) | 9 (53) |
| Yes | 10.5 (55) | 8.5 (45) | 4.5 (41) | 6.5 (59) | 15 (54) | 13 (46) |
| | p = 0.71 | | p = 1 | | p = 0.76 | |
| Atopy | | | | | | |
| No | 4 (44) | 5 (56) | 3 (50) | 3 (50) | 7 (50) | 7 (50) |
| Yes | 11.5 (52) | 10.5 (48) | 6.5 (50) | 6.5 (50) | 18 (55) | 15 (45) |
| | p = 1 | | p = 1 | | p = 1 | |

All p-values are exact. No significant association of the transmission of the A allele with the child's asthma or atopic state was observed, whether transmission was from the father, the mother or either parent.

Continuous Variables

The p-values from the t-test and Wilcoxon rank-sum tests for the continuous variables are shown below. The p-values from the Wilcoxon rank-sum test are shown in parenthesis. Both tests measured the association of Ige levels with the transmission of an A allele versus a C allele. In all cases, larger values of the variable were associated with transmission of the C allele.

| Continuous Variables (British) | | | |
|---|---|---|---|
| | Fathers | Mothers | All |
| lige | 0.12 (0.07) | 0.22 (0.23) | 0.06 (0.05) |
| dige | 0.11 (0.10) | 0.54 (0.75) | 0.10 (0.10) |
| iger | 0.13 (0.10) | 0.51 (0.75) | 0.12 (0.10) |
| psti | 0.05 (0.13) | 0.22 (0.19) | 0.02 (0.05) |
| rasti | 0.09 (0.21) | 0.12 (0.11) | 0.03 (0.06) |

The data suggest an association of several variables with the allele transmitted by the father, as compared to that transmitted by the mother. The p-values for fathers are lower (more significant) than the p-values for mothers for all variables with the exception of rasti. Interestingly, the p-values for the "all" category, albeit still marginal, are lower than the separate p-values for fathers and for mothers. If there were a difference for fathers, but not mothers, one would expect the "all" p-values to be higher than the fathers' p-values, as the inclusion of the mothers would dilute the effect. This is not the case here. In general, the data suggest that there may be a stronger association with the allele transmitted by the father as compared to that transmitted by the mother.

2. Australian Data:

The Australian study population contained 76 informative trios in 88 pedigrees. Of these, 9 had two heterozygous parents, 27 had a heterozygous father and 40 had a heterozygous mother only. The genotype distribution is shown, below.

| Genotype Distribution (Australian) | | | | | |
|---|---|---|---|---|---|
| | CC (%) | AC (%) | AA (%) | NA* | total |
| men | 164 (82) | 31 (15) | 6 (3) | 7 | 208 |
| women | 146 (77) | 42 (22) | 2 (1) | 3 | 193 |
| total | 310 (79) | 73 (19) | 8 (2) | 10 | 401 |

* NA: genotype not available

Discrete Variables

The categorical disease variables considered in the Australian population were asthma, wheeze, and atopy. The allele transmissions from heterozygote parents are summarized in the table, below. Both the number (#) and proportion (%) are shown. The "all" category is as defined for the British data, above.

| Transmissions from Heterozyogous Parents (Australian) | | | | | | |
|---|---|---|---|---|---|---|
| | Fathers | | Mothers | | All | |
| | A # (%) | C # (%) | A # (%) | C # (%) | A # (%) | C # (%) |
| All Children | 17.5 (49) | 18.5 (51) | 16.5 (34) | 32.5 (66) | 31 (41) | 45 (59) |
| Asthma | | | | | | |
| No | 10 (50) | 10 (50) | 10 (29) | 24 (71) | 19 (39) | 30 (61) |
| Yes | 7.5 (50) | 7.5 (50) | 6.5 (46) | 7.5 (54) | 12 (46) | 14 (54) |
| | p = 1 | | p = 0.32 | | p = 0.62 | |
| Wheeze | | | | | | |
| No | 6.5 (41) | 9.5 (59) | 8.5 (31) | 18.5 (69) | 14 (36) | 25 (64) |
| Yes | 11 (55) | 9 (45) | 8 (36) | 14 (64) | 17 (46) | 20 (54) |
| | p = 0.50 | | p = 0.76 | | p = 0.48 | |
| Atopy | | | | | | |
| No | 1 (50) | 1 (50) | 1 (25) | 3 (75) | 2 (40) | 3 (60) |
| Yes | 15.5 (47) | 17.5 (53) | 14.5 (35) | 26.5 (65) | 27 (41) | 39 (59) |
| | p = 1 | | p = 1 | | p = 1 | |

Continuous Variables

The p-values from the t-test and Wilcoxon rank-sum tests for the continuous variables are shown below. The p-values from the Wilcoxon rank-sum test are shown in parenthesis. Both tests measured the association of Ige levels with the transmission of an A allele versus a C allele. In all cases, larger values of the variable were associated with transmission of the C allele.

| Continuous Variables (Australian) | | | |
|---|---|---|---|
| | fathers | mothers | all |
| lige | 0.10 (0.05) | 0.73 (0.67) | 0.43 (0.34) |
| dige | 0.10 (0.09) | 0.64 (0.74) | 0.43 (0.48) |
| iger | 0.09 (0.06) | 0.61 (0.65) | 0.42 (0.35) |
| psti | 0.11 (0.30) | 0.09 (0.11) | 0.06 (0.14) |
| rasti | 0.28 (0.40) | 0.09 (0.08) | 0.09 (0.11) |
| lnslope | 0.97 (1.00) | 0.82 (0.72) | 0.87 (0.82) |
| lneos | 0.78 (0.87) | 0.53 (0.55) | 0.57 (0.62) |

The data suggest an association of several variables with the allele transmitted. P-values are marginal significant for both mothers and fathers for psti and rasti. For lige, dige and iger, p-values are marginal for fathers.

3. Grouped Data:
Discrete Variables

The association of the allele transmitted with atopy was further analyzed using the combined data. The results are shown below.

| | Transmissions from Heterozygote Parents (Combined) | | | | | |
|---|---|---|---|---|---|---|
| | Fathers | | Mothers | | All | |
| | A #(%) | C #(%) | A #(%) | C #(%) | A #(%) | C #(%) |
| All children | 33 (50) | 34 (50) | 26 (50) | 42 (50) | 56 (53) | 67 (47) |
| Atopy | | | | | | |
| No | 5 (50) | 6 (50) | 4 (25) | 6 (75) | 9 (40) | 10 (60) |
| Yes | 27 (47) | 28 (53) | 21 (35) | 33 (65) | 45 (41) | 54 (59) |
| | p = 1 | | p = 1 | | p = 1 | |

As noted above, the data for the discrete variables in the individual populations, including atopy, are consistent with the absence of a genetic effect, whereas the data for the continuous variables suggest a genetic effect. The continuous variables relate to the IgE response and were used in scoring an individual as atopic. The lack of an observed genetic effect, even in the combined data, may result from the low number of non-atopic children of heterozygous parents in the study population, rather than an actual absence of genetic effect. The methods used to analyze the continuous variables are less affected by the low number of individuals in this category and, thus, are likely to have a greater power to identify a genetic effect.

Continuous Variables

The p-values for the t-test and Wilcoxon rank-sum tests for the continuous variables from the combined data are shown below. The p-values from the Wilcoxon rank-sum test are shown in parenthesis. Both tests measured the association of Ige levels with the transmission of an A allele versus a C allele. In all cases, larger values of the variable were associated with transmission of the C allele.

| | Continuous Variables (Combined) | | |
|---|---|---|---|
| | fathers | mothers | all |
| lige | 0.02 (0.01) | 0.14 (0.17) | 0.03 (0.02) |
| dige | 0.02 (0.01) | 0.37 (0.39) | 0.05 (0.04) |
| iger | 0.02 (0.01) | 0.34 (0.30) | 0.06 (0.02) |
| psti | 0.04 (0.10) | 0.02 (0.03) | 0.004 (0.01) |
| rasti | 0.10 (0.13) | 0.01 (0.01) | 0.004 (0.01) |

The combined data indicate that there are significant associations of the TCF-1 allele with variable values. The data suggest a significant effect in both genders for psti and rasti. There is also a significant effect for the allele transmitted from fathers, but not for allele transmitted from mothers, for lige, dige, and iger.

Conclusions:

The British data appear to be consistent with an absence of genetic effects contributing to the presence or absence of asthma and atopy. The data suggest a genetic effect on specific measures of the IgE response, as measured by the continuous variables. The data suggest that there is an association between the allele transmitted from the heterozygous parent of either sex on psti and rasti, and between the allele transmitted from the heterozygous father on lige, dige and iger.

The pattern for the Australian data is similar to that for the British data. The data appear to be consistent with an absence of genetic effects contributing to the presence or absence of asthma, wheeze, and atopy. The data suggest a genetic effect on specific measures of the IgE response. There appears to be a significant association between the allele transmitted from the heterozygous parent of either sex on psti and rasti, and between the allele transmitted from the heterozygous father on lige, dige and iger.

The trends seen in the individual populations are more strongly indicated by the combined data. As with the separate population data, the combined data also appear to be consistent with an absence of genetic effects contributing to the presence or absence of atopy. However, the combined data more strongly indicate that there are significant associations of the TCF-1 allele transmitted with the specific measures of the IgE response. The combined data indicate a significant association between the allele transmitted from the heterozygous parent of either sex on psti and rasti, and between the allele transmitted from the heterozygous father on lige, dige and iger. The association is between the C allele and an increased IgE response.

As noted above, asthma is a poorly defined disease which may have multiple etiologies, including disease not associated with the atopic state. As TCF-1 is part of the pathway affecting IgE production, it can be hypothesized that any effect of the TCF-1 allele would be manifest only in Th2-mediated inflammatory diseases, such as atopic asthma, and that the allele effect would not play a role in other forms of asthma. The data present herein, which indicate an association of the TCF-1 allele with IgE response even though no effect on asthma, as imprecisely defined herein, is apparent, are consistent with this hypothesis.

The significant association of the TCF-1 allele with IgE response indicates that genotyping at the TCF-1 locus may provide useful information in characterizing the likelihood of atopic asthma and other Th2-mediated inflammatory diseases. In particular, the data indicate that individuals who have received a paternal C allele are more likely to mount an elevated IgE response and may indicate that the individual is at increased risk of a Th2-mediated disease.

Because of the complex and still largely unknown genetic basis of asthma and inflammatory diseases in general, it is expected that additional loci will be identified that affect the likelihood of a Th2-mediated disease. It is expected that the TCF-1 genotype will be more informative in combination with genotype information at one or more other loci determined to be associated with Th2-mediated disease.

We claim:

1. A method for characterizing an individual as possessing a factor contributing to an increased risk of type 1 diabetes or multiple sclerosis comprising:
   (a) determining the genotype of said individual with respect to the nucleotide present at position 883 of the TCF-1 gene;
   (b) classifying said individual based on the result obtained from step (a), wherein the presence of an A allele indicates a factor contributing to an increased risk of type 1 diabetes or multiple sclerosis.

2. A method for determining the genotype of a sample comprising a nucleic acid with respect to the nucleotide present in a TCF-1 gene at position 883, comprising:
   (a) contacting the nucleic acid with an oligonucleotide probe exactly complementary to an A allele or a C allele in a region encompassing position 883 under conditions such that hybridization occurs if and only if the A allele or the C allele is present; and
   (b) detecting if hybridization occurs, wherein, hybridization to the A allele indicates that the genotype of the sample corresponds to the A allele and hybridization to the C allele indicates that the genotype of the sample corresponds to the C allele.

3. The method of claim 2, wherein the region encompassing position 883 is amplified prior to, or concurrent with step (a).

4. A method of claim 3, wherein said probe is selected from the group consisting of KW196 (SEQ ID NO: 8) orKW118 (SEQ ID NO: 9).

5. A method for determining the genotype of a sample comprising a nucleic acid with respect to the nucleotide present in a TCF-l gene at position 883, comprising:
   (a) contacting the nucleic acid with one or more allele-specific primers specific for an A allele or a C allele under amplification conditions such that amplification occurs using said allele-specific primer if and only if the A allele or the C allele is present; and
   (b) detecting if amplifications occurs, wherein, amplification of the A allele indicates that the genotype of the sample corresponds to the A allele and amplification of the C allele indicates that the genotype of the sample corresponds to the C allele.

6. A method of claim 5, wherein said allele specific primer is GZ351B (SEQ ID NO: 4) or GZ374B (SEQ ID NO: 5).

7. The method of claim 1, wherein said TCF-1 gene comprises SEQ ID NO: 1, an A allele of SEQ ID NO: 1 or the complements thereof.

8. A method for determining the presence of an A allele or a C allele of a TCF-1 gene in a sample comprising a nucleic acid, comprising:
- (a) contacting the nucleic acid with an oligonucleotide exactly complementary to the A allele or the C at position 883 under stringent hybridization conditions; and
- (b) detecting hybridization wherein, hybridization to the A allele indicates the presence of the A allele and hybridization to the C allele indicates the presence of the C allele.

9. A method for characterizing an individual as possessing a factor contributing to an increased likelihood of having an increased IgE response comprising:
- (a) determining the genotype of said individual with respect to the nucleotide present at position 883 of the TCF-1 gene;
- (b) classifying said individual based on the result obtained from step (a), wherein the presence of a C allele indicates a factor contributing to an increased likelihood of having an increased IgE response.

10. The method of claim 9 wherein said TCF-1 gene comprises SEQ ID NO: 1, an A allele of SEQ ID NO: 1 or the complements thereof.

11. The method of claim 9, wherein said increased IgE response is associated with atopy or allergic asthma.

* * * * *

SEQUENCE LISTING

<160> NUMBER OF SEQ ID NOS: 9

<210> SEQ ID NO 1
<211> LENGTH: 2855
<212> TYPE: DNA
<213> ORGANISM: Homo sapiens
<220> FEATURE:
<221> NAME/KEY: misc_feature
<222> LOCATION: 426
<223> OTHER INFORMATION: n=a,t,g, or c

<400> SEQUENCE: 1

| | | | | | |
|---|---|---|---|---|---|
| ggatcccggg | ggtcccgggg | gccggcgccg | gggcccgcgg | cgaggccgag | gtgagccccc | 60 |
| gccggcgccg | gctcctcccc | cgcggtcgcc | gcccgcgccg | ccccagttgc | gcgccgccct | 120 |
| cggggtctcc | agacagagcg | tccctgcccc | ggcgtcggcc | ccgaccccg | cggtcccacc | 180 |
| gcccctcact | cccctccggt | tctccctcca | ggctctcggg | cgggaacacc | gtgcgcagag | 240 |
| actcttcccg | gacaaacttc | cagagcccct | ggaggacggt | gagtttctgc | ccggcccggc | 300 |
| ttcccttcgt | cgcgctcagg | ccctggcctc | ggtgggacgg | ggacgccaag | gaccgcgggg | 360 |
| agccgggtgc | ctcccccacc | gcagctcagg | aggcggcaga | acccaggggt | ggagagtggg | 420 |
| gggcgngctt | cccgggcgcc | gccgggtcga | gtcacttccg | gtgccctgac | ctttatagga | 480 |
| gtaaacagac | ccccgccatc | cccgcctccc | ctcctgccca | ggtgactgac | taatccgccg | 540 |
| ccttcaggag | acagaattgg | ccaaggtttc | ttggttggag | ggtgggggt | gggaggtcaa | 600 |
| gtagggcca | cctcggggag | gcctgccctc | caggtccttc | ccctaaaact | tggcactgcc | 660 |
| gatactccca | gcccgttcct | tcccaagtca | ggaacttgca | ggggacccct | tggcaattct | 720 |
| ttttctctca | agagcagaca | gccttcagtc | ccagccgctg | ccagggctgg | tgtgtctgac | 780 |
| ccagctgtgg | ttttttccagg | cctgaaggcc | ccggagtgca | ccagcggcat | gtacaaagag | 840 |
| accgtctact | ccgccttcaa | tctgctcatg | cattacccac | cccctcgggg | agcagggcag | 900 |
| caccccagc | cgcagccccc | gctggtaagt | ggaccccgcc | actcacccac | cctccttctc | 960 |
| atttttcagc | acaaggccaa | tcagccccc | cacggtgtcc | cccaactctc | tctctacgaa | 1020 |
| catttcaaca | gcccacatcc | cacccctgca | cctgcggaca | tcagccagaa | gcaaggtaca | 1080 |
| agcctgggat | gcccactcac | tcagcttctc | tcctctgcag | ttcacaggcc | tctgcagacc | 1140 |
| cctgacctct | ctggcttcta | ctccctgacc | tcaggcagca | tggggcagct | ccccccacact | 1200 |
| gtgagctggt | gagtgtgggc | ccagctcagt | gttaactttc | ttcctgcctc | caggttcacc | 1260 |
| cacccatcct | tgatgctagg | ttctggtgta | cctggtcacc | cagcagccat | cccccacccg | 1320 |
| gccattgtgc | cccctcagg | gaagcaggag | ctgcagccct | tcgaccgcaa | cctgtgagtg | 1380 |
| aaagacaatc | ctgaacaatc | tggatttgtg | ccctcagga | agacacaagc | agagtccaag | 1440 |
| gcagagaagg | aggccaagaa | gccaaccatc | aagaagcccc | tcaatgcctt | catgctgtac | 1500 |
| atgaaggaga | tgagagccaa | ggtcattgca | gagtgcacac | ttaaggagag | cgctgccatc | 1560 |
| aaccagatcc | tgggccgcag | ggtgagacca | tgggcaggtg | ggctggcagg | gatgctcccc | 1620 |
| gaccatcttc | agcctggtgc | agcctgctga | ctccctgatg | cacccacct | gcccctcttc | 1680 |
| cctgttgcag | tggcacgcgc | tgtcgcgaga | agagcaggcc | aagtactatg | agctggcccg | 1740 |
| caaggagagg | cagctgcaca | tgcagctata | cccaggctgg | tcagcgcggg | acaactacgt | 1800 |
| gagtgcctag | tgtctgagca | tccctccttt | tgttccctgc | aggggaagaa | gaagaggcgg | 1860 |
| tcgagggaaa | agcaccaaga | atccaccaca | ggtgagacct | tctctcgctc | taccctctg | 1920 |

-continued

```
gcatggctgt gagcagaccc tggctcgcct aagaaatgcc gtgctcgctt tggcctcaac    1980
cagcagacgg attggtgtgg tccgtgcagg tgggtttgtc cccagggaa gttctattcc     2040 attcattcca tcagagacaa actggcccag agaactcaag gatggtaatg acaagagtc     2100 actgtccatg tcttcttcct ctagcccagc ttgaggactg ggatggctgg gcaaggaagc    2160
cataggcatt gcggcccctt gccttggtgc agatgtgagt cccacaaaca catctggaga   2220
agctcaaagg ccgggactgg gagatgactc ccttggaaga caggagagat gactcccttg    2280
gaagacagat gacagcccat aggcctagtg acaaaaggcc cctttgggac cttgtggctg    2340
ttctgggaac tgcacctgtc ctaggtctgg gccagaccaa gcagaatggc agtctgagga   2400
cactgactta ccacccaagt cccaggaaga gaggacaagg aatcagccag gcctgtgcaa    2460
aggcagcatt ttttggttgt ggtgtatgac tatgaattca ccctctgttt acagataact    2520
ctcttcacta ttcctaggag gaaaagaaa tgcattcggt acttacccgg agaaggccgc     2580
tgccccagcc ccgttccttc cgatgacagt gctctaggct gccccgggtc cccagctccc   2640
caggactcac cctcatacca tctgctgccc cgcttcccca cagaactgct tactagccct    2700 gaaaagatt attgtagtgt tcaaaatatt tttgtattgt taatgcatca tcatagaaaa     2760
acttttaaac atgagaataa agatacttt tactgggttt gttttttcaaa gcctgacccct  2820 gaggaataag ctgtttcagt aacagagcat gatat                                2855
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2
ccaggtcctt cccctaa                                                     17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
tccaggtcct tccctaaaa                                                  20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 4
catgcattac ccaccca                                                    17

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 5
```

-continued

```
cctgctcccg aggg                                              14

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
gcggggtcca cttacca                                           17

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
tactccgcct tcaatctgct ca                                     22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Probe

<400> SEQUENCE: 8
attacccacc ccctcggga                                         20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 9
ccgaggtggg tgggtaat                                          18
```